(12) United States Patent
Kim

(10) Patent No.: US 11,931,376 B1
(45) Date of Patent: Mar. 19, 2024

(54) METHODS FOR THE TREATMENT OF CHRONIC KIDNEY DISEASE

(71) Applicant: RENATUS INC., Wonju-si (KR)

(72) Inventor: Hee Gon Kim, Wonju-si (KR)

(73) Assignee: RENATUS INC., Wonju-si (KR)

( * ) Notice: Subject to any disclaimer, the term of this patent is extended or adjusted under 35 U.S.C. 154(b) by 0 days.

(21) Appl. No.: 18/314,962

(22) Filed: May 10, 2023

Related U.S. Application Data

(60) Provisional application No. 63/404,740, filed on Sep. 8, 2022.

(51) Int. Cl.
*A61K 31/724* (2006.01)
*A61P 13/12* (2006.01)

(52) U.S. Cl.
CPC ............ *A61K 31/724* (2013.01); *A61P 13/12* (2018.01)

(58) Field of Classification Search
CPC .............................. A61K 31/724; A61P 13/12
See application file for complete search history.

(56) References Cited

U.S. PATENT DOCUMENTS

| | | | |
|---|---|---|---|
| 10,869,884 B2 * | 12/2020 | Kulkarni | ............ A61K 31/724 |
| 2013/0005684 A1 | 1/2013 | Fichert et al. | |
| 2017/0216342 A1 | 8/2017 | Era et al. | |
| 2019/0209605 A1 | 7/2019 | Kulkarni et al. | |
| 2020/0268788 A1 | 8/2020 | Wittkowski | |

FOREIGN PATENT DOCUMENTS

| | | | |
|---|---|---|---|
| CA | 3 037 286 A1 | 3/2018 | |
| CN | 112138019 A | 12/2020 | |
| EP | 4198061 A1 * | 6/2023 | |
| JP | 2013-522330 A | 6/2013 | |
| JP | 2019-533011 A | 11/2019 | |
| KR | 10-2513011 B1 | 3/2023 | |
| WO | 2022/178318 A1 | 8/2022 | |
| WO | WO-2023033276 A1 * | 3/2023 | |

OTHER PUBLICATIONS

Mitrofanova et al., Kidney International, 2018, 94, p. 1151-1159. (Year: 2018).*
Saokham et al., International Journal of Pharmaceutics, 2017, 516, p.278-292. (Year: 2017).*
Singhal et al., Cell Death and Disease, 2018, 9:1019, 13 pages. (Year: 2018).*
Yuan, Q., et al., "Signaling pathways of chronic kidney diseases, implications for therapeutics", Signal Transduction and Targeted Therapy, Jun. 9, 2022, vol. 7, Article 182, pp. 1-27.
Merscher-Gomez, S., et al., "Cyclodextrin Protects Podocytes in Diabetic Kidney Disease", Diabetes, vol. 62, Nov. 2013, pp. 3817-3827.
Singhal, A., et al., "2-Hydroxypropyl-gamma-cyclodextrin overcomes NPC1 deficiency by enhancing lysosome-ER association and autophagy", Scientific Reports, 2020, vol. 10, Article 8663, pp. 1-14.
Frijlink, H., et al.,"The Effect of Parentally Administered Cyclodextrins on Cholesterol Levels in the Rat", Pharmaceutical Research, vol. 8, No. 1, 1991, pp. 9-16.
International Search Report (PCT/ISA/210) dated Aug. 7, 2023 issued by the International Searching Authority in International Application No. PCT/KR2023/006206.
E. Albers et al., "Cyclodextrin Derivatives in Pharmaceutics"; Critical Reviews in Therapeutic Drug Carrier Systmes, Begell House Publishing Inc, US, vol. 12, No. 4, Jan. 1, 1995, pp. 311-337, XP008112662.
National Institute of Diabetes And Digestive And Kidney Disease: "Diabetic Kidney Disease", https://www.niddk.nih.gov/health-information/diabetes/overview/preventing-problems/diabetic-kidney-disease, Jul. 28, 2020 (Jul. 28, 2020), XP093121330.
Extended European Search Report dated Jan. 29, 2024 issued by the European Patent Office in European Patent Application No. 23172543.3.

* cited by examiner

*Primary Examiner* — Jonathan S Lau
(74) *Attorney, Agent, or Firm* — Sughrue Mion, PLLC

(57) ABSTRACT

Provided are a method of treating chronic kidney disease or one or more symptoms thereof, or reducing a complication related to chronic kidney disease, the method comprising, administering a therapeutically effective amount of gamma-cyclodextrin oligomer to a subject in need thereof. The gamma-cyclodextrin oligomers are effective in cholesterol metabolism enhancement, cholesterol efflux, reducing inflammatory cytokine secretion, renal clearance of cholesterol and/or reducing albuminuria. Therefore, the gamma-cyclodextrin oligomers can be used to treat or alleviate chronic kidney disease, symptoms thereof and/or a complication related to chronic kidney disease.

24 Claims, 14 Drawing Sheets

METHODS FOR THE TREATMENT OF CHRONIC KIDNEY DISEASE

CROSS REFERENCE TO RELATED APPLICATIONS

This application is based on and claims priority from U.S. Provisional Application No. 63/404,740, filed on Sep. 8, 2022 in the U.S. Patent and Trademark Office, the disclosures of which are incorporated herein in their entirety by reference.

BACKGROUND

Chronic kidney disease (CKD) is a common disease affecting more than 1 in 7 adults, which is 15% of US adults. It is a long-term condition where the kidneys don't work as well as they should. Common causes of CKD are high blood pressure, diabetes, high cholesterol, infection, long-term use of certain medicines, and others. Whereas early detection and treatment can keep CKD from getting worse, its progression eventually leads to kidney failure. Even with dialysis treatment, an estimated 20-50% of people with end-stage renal disease die within 2 years. Mounting evidence suggests that dysregulated cholesterol homeostasis is involved in the pathogenesis of prevalent (e.g., diabetic kidney disease) and less prevalent (e.g., focal segmental glomerulosclerosis, and Alport syndrome) kidney diseases. However, currently there is no treatment that can directly target cholesterol and promote its metabolism and clearance in the kidney. As such there are great needs to develop new treatments for CKD to target the underlying mechanisms of CKD and help halt and/or reverse the disease progression.

SUMMARY

In one aspect, the present disclosure provides a method of i) treating, alleviating or reducing albuminuria, ii) reducing kidney cholesterol content, iii) improving renal clearance of cholesterol, or iv) treating, alleviating or reducing inflammation induced by cholesterol in the kidney. The method comprises administering a therapeutically effective amount of gamma-cyclodextrin oligomers to a subject in need thereof. In one embodiment, the subject may have been diagnosed with or suspected to have chronic kidney disease. In some embodiments, the level of albumin in urine is reduced by at least about 10% or greater relative to the level of albumin in urine prior to treatment with the cyclodextrin. In some embodiments, the amount of kidney cholesterol content is reduced by at least about 10% or greater relative to the amount of kidney cholesterol content prior to the treatment. In some embodiments, the treatment promotes renal clearance of cholesterol in the subject by at least 10% or greater relative to prior to the treatment. In some embodiments, the inflammation in the kidney is decreased (e.g., as measured by RNA levels, intracellular or extracellular cytokine proteins, inflammation-targeted imaging modalities) relative to the inflammation prior to the treatment. In some embodiments, the treatment reduces severity or a symptom of chronic kidney disease and/or its complications including, but not limited to, heart disease, high blood pressure, anemia, bone weakness, metabolic acidosis and electrolyte disorders, uremic symptoms, hyperkalemia, gout, or fluid retention.

In some embodiments, an effective amount of a gamma-cyclodextrin oligomer may be administered to a subject in need thereof. In some embodiments, the average molecular weight of the gamma-cyclodextrin oligomers is between about 2.5 kDa to 20 kDa. In some embodiments, the gamma-cyclodextrin oligomer comprises gamma-cyclodextrin oligomer species comprising at least 2 to at most 10 gamma-cyclodextrin monomers. In some embodiments, the gamma cyclodextrin monomer is native gamma cyclodextrin or its derivatives. In some embodiments, the derivative is hydroxypropyl-gamma-cyclodextrin. In some embodiments, the hydroxypropyl-gamma-cyclodextrin has a molar substitution value between 0.2 and 0.9. In some embodiments, the gamma-cyclodextrin oligomer is chemically modified by replacing a part of the structure (e.g., hydrogen) with another atom or a functional group. In some embodiments, the gamma-cyclodextrin oligomer comprises 10% (w/w) or less of gamma-cyclodextrin monomers.

The present disclosure also provides a method of treating chronic kidney disease and/or one or more symptoms thereof or treating a subject suspected to have chronic kidney disease and/or one or more symptoms thereof. The method comprises administering a therapeutically effective amount of gamma-cyclodextrin oligomer, to the subject, thereby treating the chronic kidney disease and/or one or more symptoms thereof in the subject. In some cases, the treating comprises alleviating or reducing albuminuria by at least 10% or greater in the subject. In some cases, kidney cholesterol content is reduced by at least 10% or greater in the subject. In some cases, renal clearance of cholesterol is increased by at least 10% or greater in the subject. In some cases, the inflammation in the kidney is decreased (e.g., as measured by RNA levels, intracellular or extracellular cytokine proteins, inflammation-targeted imaging modalities) relative to the inflammation prior to the treatment.

In any one of the preceding aspects, the therapeutically effective amount is from about 20 mg/kg to 4,000 mg/kg. In some instances, the therapeutically effective amount is from about 1 g to about 200 g. In any one of the preceding aspects, the therapeutically effective amount is an amount sufficient to achieve a serum, plasma, and/or whole blood concentration of gamma cyclodextrin oligomers of about 0.01 mg/ml to about 20 mg/ml. In any one of the preceding aspects, the administering is by parenteral methods including intravenous, subcutaneous, intravascular, intramuscular, intrathecal, depot, peristaltic pump administration. In any one of the preceding aspects, the therapeutically effective amount may be administered by a device (e.g., wearable injection systems).

In any one of the preceding aspects, the administering comprises: (i) administering, at a first time point, a therapeutically effective amount of gamma-cyclodextrin oligomer to the subject; and (ii) administering, at a second time point, a therapeutically effective second dose of gamma-cyclodextrin oligomer to the subject. In any one of the preceding aspects, the second time point is at least 6 hours, at least 12 hours, at least 1 day, at least 2 days, at least 3 days, at least 4 days, at least 5 days, at least 6 days, at least a week, at least 2 weeks, at least 3 weeks, at least 4 weeks, at least 2 months, at least 3 months, at least 6 months, or at least 12 months after the first time point. In any one of the preceding aspects, the administering comprises administering every day, every 3 days, every 7 days, every 10 days, every 14 days, every 21 days, every 28 days, every 2 months, every 3 months, every 6 months, every 12 months.

The present disclosure also provides a method of i) reducing ACE inhibitors, ARBs, Cis, or steroids, ii) reducing a frequency or delaying renal replacement therapy (e.g., hemodialysis, peritoneal dialysis, hemofiltration, and/or hemodiafiltration), or iii) delaying kidney transplant in a subject with or suspected to have chronic kidney disease, comprising: administering a therapeutically effective amount of gamma-cyclodextrin oligomer to the subject, thereby treating chronic kidney disease and/or one or more symptoms thereof in the subject.

In some embodiments, the average molecular weight of the gamma-cyclodextrin oligomers is between about 2.5 kDa to 20 kDa. In some embodiments, the therapeutically effective amount is from about 1 g to about 200 g. In some embodiments, the therapeutically effective amount is an amount sufficient to achieve a serum, plasma, and/or whole blood concentration of gamma cyclodextrin oligomers of about 0.01 mg/ml to about 20 mg/ml. In some embodiments, ACE inhibitors, ARBs, CIs, or steroids treatment is reduced at least by 20% compared to before administering the gamma-cyclodextrin oligomer. In some embodiments, the frequency of renal replacement therapy is reduced at least by 20% compared to before administering the gamma-cyclodextrin oligomer. In some embodiments, the initiation of renal replacement therapy is delayed at least 6 months. In some embodiments, a kidney transplant is delayed at least 6 months.

In some instances, the administering comprises: (i) administering, at a first time point, a therapeutically effective amount of gamma-cyclodextrin oligomer to the subject; and (ii) administering, at a second time point, a therapeutically effective second dose of gamma-cyclodextrin oligomer to the subject. In any one of the preceding aspects, the second time point is at least 6 hours, at least 12 hours, at least 1 day, at least 2 days, at least 3 days, at least 4 days, at least 5 days, at least 6 days, at least a week, at least 2 weeks, at least 3 weeks, at least 4 weeks, at least 2 months, at least 3 months, at least 6 months, or at least 12 months after the first time point.

In another aspect, the present disclosure provides a pharmaceutical composition comprising a sufficient amount of gamma-cyclodextrin oligomer to treat, alleviate or reduce albuminuria, kidney cholesterol content, promote renal clearance of cholesterol, and/or treat, alleviate or reduce inflammation in the kidney in a subject diagnosed with or suspected to have chronic kidney disease, and a pharmaceutically acceptable excipient.

In another aspect, the present disclosure provides a pharmaceutical composition comprising a sufficient amount of gamma-cyclodextrin oligomer to treat chronic kidney disease and/or one or more symptoms of chronic kidney disease, and a pharmaceutically acceptable excipient.

In another aspect, the present disclosure provides the pharmaceutical composition formulated for single dose or repeated administration. In any one of the preceding aspects, the pharmaceutical composition is formulated for parenteral methods of administration including intravenous, intravascular, subcutaneous, intramuscular, intrathecal, depot, and peristaltic pump administration. In any one of the preceding aspects, the therapeutically effective amount may be administered by a device (e.g., wearable injection systems).

In another aspect, the present disclosure provides a gamma-cyclodextrin oligomer for use in treating chronic kidney disease or one or more symptoms thereof, or reducing a complication related to chronic kidney disease.

In some embodiments, the treating chronic kidney disease or one or more symptoms thereof comprises i) treating, alleviating or reducing albuminuria, ii) reducing an amount of kidney cholesterol, iii) improving renal clearance of cholesterol, and/or iv) treating, alleviating or reducing inflammation in kidney of the subject.

In some embodiments, the gamma-cyclodextrin oligomer reduce a level of albumin or albumin to creatinine ratio in urine by at least about 10% relative to a level of albumin or albumin to creatinine ratio in urine prior to administering the gamma-cyclodextrin oligomer.

In some embodiments, the gamma-cyclodextrin oligomer reduce the amount of kidney cholesterol by at least 10% relative to the amount of kidney cholesterol prior to administering the gamma-cyclodextrin oligomer.

In some embodiments, the gamma-cyclodextrin oligomer improve the renal clearance of cholesterol by at least about 10% relative to renal clearance of cholesterol prior to administering the gamma-cyclodextrin oligomer.

In some embodiments, an average molecular weight of the gamma-cyclodextrin oligomer is between 2.5 kDa to 20 kDa.

In some embodiments, the gamma-cyclodextrin oligomer comprises gamma-cyclodextrin oligomer species containing at least 2 and at most 10 gamma-cyclodextrin monomers.

In some embodiments, the gamma-cyclodextrin monomer comprises gamma-cyclodextrin or its derivatives.

In some embodiments, the gamma cyclodextrin derivative comprises hydroxypropyl-gamma cyclodextrin.

In some embodiments, the hydroxypropyl-gamma-cyclodextrin has molar substitution value between 0.2 and 0.9.

In some embodiments, the gamma-cyclodextrin oligomer is administered a therapeutically effective amount of gamma-cyclodextrin oligomer to a subject in need thereof, wherein the subject has been diagnosed with or suspected to have a chronic kidney disease.

In some embodiments, the therapeutically effective amount is from about 20 mg/kg to about 4,000 mg/kg, or from about 1 g to about 200 g.

In some embodiments, the administering further comprises: (i) administering, at a first time point, a therapeutically effective first dose of gamma-cyclodextrin oligomer to the subject; and (ii) administering, at a second time point, a therapeutically effective second dose of gamma-cyclodextrin oligomer to the subject.

In some embodiments, the second time point is at least 6 hours, at least 12 hours, at least 1 day, at least 2 days, at least 3 days, at least 4 days, at least 5 days, at least 6 days, at least a week, at least 2 weeks, at least 3 weeks, at least 4 weeks, at least 2 months, at least 3 months, at least 6 months, or at least 12 months after the first time point.

In some embodiments, the administering further comprises administering every day, every 3 days, every 7 days, every 10 days, every 14 days, every 21 days, every 28 days, every 2 months, every 3 months, every 6 months, every 12 months.

DETAILED DESCRIPTION OF THE DISCLOSURE

Figure 1A:
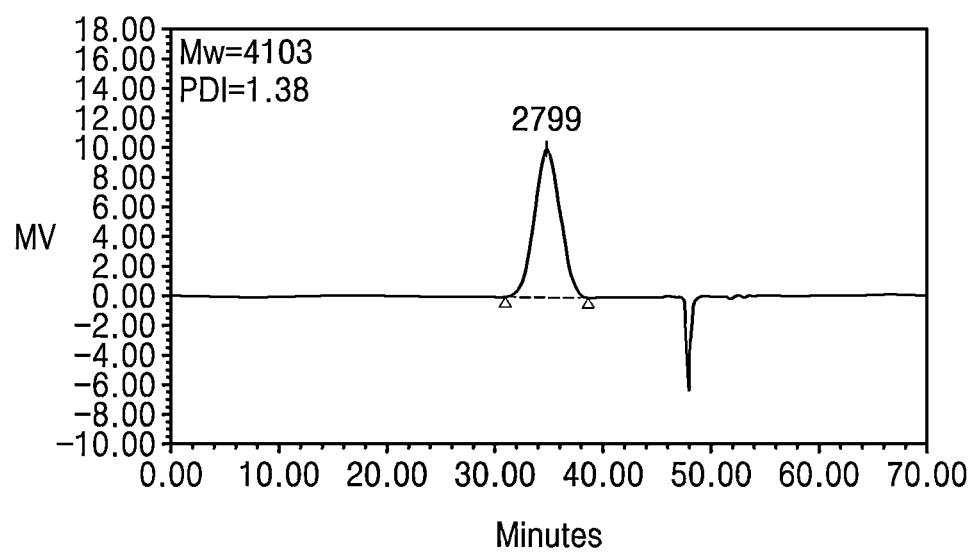
FIG. 1A and FIG. 1B show gel permeation chromatographs of gamma-cyclodextrin oligomers consisted of gamma-cyclodextrin monomers (A, Oligo-GCD) and hydroxypropyl-gamma-cyclodextrin monomers (B, Oligo-HPGCD).

Chronic kidney disease (CKD) affects more than 38 million people in the United States. chronic kidney disease can be classified based on glomerular filtration rate and albuminuria. Albuminuria-based stages include A1 (<30 mg/day, normal to mildly increased), A2 (30 to 300 mg/day, moderately increased), and A3 (>300 mg/day, severely increased). Glomerular filtration rate (GFR)-based stages include G1 (>90 mL/min/1.73 m$^2$, normal or high), G2 (60-89 mL/min/1.73 m$^2$, mildly decreased), G3a (45-59 mL/min/1.73 m$^2$, mildly to moderately decreased), G3b (30-44 mL/min/1.73 m$^2$, moderately to severely decreased), G4 (15-29 mL/min/1.73 m$^2$, severely decreased), and G5 (<15 mL/min/1.73 m$^2$, kidney failure). GFR is a measure of kidney function; albuminuria is a marker of kidney damage.

Angiotensin-converting enzyme (ACE) inhibitors or angiotensin II receptor blockers (ARBs) are commonly used in chronic kidney disease patients. The agents target and dilate arterioles to promote renal blood flow and glomerular filtration. Steroids or calcineurin inhibitors (CI) target and reduce inflammation in chronic kidney disease patients.

Mounting evidence suggests that accumulation of cholesterol in the kidney causes pathogenesis and progression of chronic kidney disease. Dysregulated cholesterol homeostasis is observed in prevalent (e.g., diabetic kidney disease), as well as in less prevalent (e.g., focal segmental glomerulosclerosis and Alport syndrome) kidney diseases. However, there is no treatment that can directly target cholesterol and promote its metabolism and clearance.

Cyclodextrins are cyclic oligosaccharides that have shown to form complexes with hydrophobic molecules including cholesterol due to their unique structure. One of its derivatives, hydroxypropyl-beta-cyclodextrin, is in clinical trials for the treatment of varying cholesterol-driven diseases including Niemann-Pick Type C, and Alzheimer's disease. However, hydroxypropyl-beta-cyclodextrin can cause disruption of plasma membrane via cholesterol extraction thereof, which can lead to its dose-limiting side effect, ototoxicity, in a subject. Furthermore, hydroxypropyl-beta-cyclodextrin and some other cyclodextrins are known to cause vacuolation of kidney tubular cells, implying its potential toxicity in the kidney. Therefore, use of cyclodextrins that can improve cholesterol metabolism and clearance and exhibits low plasma membrane disruption has the potential to improve the safety and efficacy of the drug for the treatment of cholesterol-driven diseases including chronic kidney disease.

Disclosed herein are methods for alleviating or reducing albuminuria, reducing an amount of kidney cholesterol, improving renal clearance of cholesterol, and/or alleviating or reducing inflammation induced by cholesterol in the kidney in a subject. In some cases, the methods involve treating chronic kidney disease (e.g., by slowing down, halting, or reversing the progression of chronic kidney disease, including alleviating or reducing albuminuria and/or improving glomerular filtration rate). In some cases, the methods involve treating a symptom, and/or clinical manifestations of chronic kidney disease. In some cases, the methods involve treating the complications of chronic kidney disease. In some cases, the methods involve reducing inflammation (e.g., as measured by RNA levels, intracellular or extracellular cytokine proteins, inflammation-targeted imaging modalities) in the kidney or other organs. In some cases, the methods involve reducing ACE inhibitors, ARBs, CIs, or steroids, and/or reducing a frequency or delaying renal replacement therapy and/or delaying a kidney transplant.

Generally, the methods provided herein involve administering a therapeutically effective amount of gamma-cyclodextrin oligomer to a subject in need thereof. In some cases, the average molecularweight of the gamma cyclodextrin oligomer is between 2.5 kDa to 20 kDa. In some cases, the gamma-cyclodextrin oligomer comprises gamma-cyclodextrin oligomer species comprising at least 2 and at most 10 gamma cyclodextrin monomers. In some cases, the gamma cyclodextrin monomer is gamma cyclodextrin or its derivatives. In some cases, the derivative is hydroxypropyl-gamma-cyclodextrin. In some embodiments, the gamma-cyclodextrin oligomer is chemically modified by replacing a part of the structure with another atom or a functional group. In some embodiments, the gamma-cyclodextrin oligomer composition comprises 10% (w/w) or less of gamma-cyclodextrin monomers.

In one aspect, the gamma-cyclodextrin oligomer exhibits significantly low plasma membrane disruption by cholesterol extraction, which in turn significantly lowers its cellular toxicity and hemolysis. For example, the gamma-cyclodextrin oligomer induces plasma membrane cholesterol extraction and hemolysis reduced by at least 20% or greater relative to hydroxypropyl-beta-cyclodextrin. In one aspect, the gamma-cyclodextrin oligomer exhibits effective dissolution of cholesterol crystals. For example, the gamma-cyclodextrin oligomer dissolves cholesterol crystals increased by at least 20% or greater relative to hydroxypropyl-beta-cyclodextrin. In one aspect, the gamma-cyclodextrin oligomer increases cellular expression of ATP Binding Cassette Subfamily A Member 1 (ABCA1), which plays crucial roles in transporting cholesterol out of cells. For example, the gamma-cyclodextrin oligomer induces cellular ABCA1 expression increased by at least 10% or greater relative to hydroxypropyl-beta-cyclodextrin.

1. Definitions

The articles "a" and "an" are used in this disclosure to refer to one or more than one (e.g., at least one) of the grammatical object of the article, unless the context clearly dictates otherwise. By way of example, "an element" means one element or more than one element.

The term "and/or" is used in this disclosure to mean either "and" or "or" unless indicated otherwise.

The terms "subject," "individual," and "patient" are used interchangeably and include any animal, including mammals, e.g., humans, mice rats, rabbits, dogs, cats, swine, cattle, sheep, horse, or other primates.

The term "about" a number refers to that number plus or minus 10 of that number. The term "about" a range refers to that range plus 10% of its greatest value and minus 10% of its lowest value.

The terms "treat," "treating," or "treatment," or other grammatical equivalents include any effect, for example, alleviating, reducing, modulating, ameliorating, or eliminating, that results in the improvement of the condition, disease, disorder, and the like, or alleviating one or more symptoms thereof. Treating can be curing, improving, or at least partially ameliorating the disorder. In certain embodiments, treating is curing the disease.

The term "pharmaceutically acceptable" includes molecular entities and formulations that are generally safe, non-toxic, and neither biologically nor otherwise undesirable and is acceptable for pharmaceutical use in humans and non-human animals.

The term "pharmaceutically acceptable excipient" and "pharmaceutically acceptable carrier" refer to a substance that helps the administration of an active ingredient to and absorption by a subject and can be included in the compositions of the present disclosure without causing a significant adverse effect in the patient. Non-limiting examples of pharmaceutically acceptable excipients include water, NaCl, saline solutions, alcohols, oils, gelatins, carbohydrates such as lactose, amylose or starch, fatty acid esters, hydroxyethyl cellulose, polyvinyl pyrrolidine, and colors, and the like.

The terms "effective amount" or "therapeutically effective amount" refer to the amount of a compound or composition sufficient to effect beneficial or desired results. An effective amount can be administered in one or more administration, applications, or dosages and is not intended to be limited to a particular formulation or administration route.

The gamma-cyclodextrin defined in the present specification is a cyclic oligosaccharide in which eight glucopyranose units are bonded by α-(1,4)-glycosidic bonds and may include gamma-cyclodextrin and a derivative thereof.

The term "derivative" refers to a compound obtained by substituting a part of a structure of cyclodextrin, particularly, a hydroxyl group of C2, C3, or C6, with another atom or atomic group. A derivative may be induced by replacing at least one hydrogen in an unsubstituted mother group with another atom or a functional group.

The term "substituted" refers to that a part of a structure of cyclodextrin (e.g., hydrogen) is substituted with at least one substituent selected from halides, C1-C40 alkyl groups, C2-C40 alkenyl groups, C2-C40 alkynyl groups, C3-C40 cycloalkyl groups, C3-C40 cycloalkenyl groups, and C7-C40 aryl groups. When it is stated as a functional group is "selectively substituted", it means that the functional group may be substituted with the above substituent.

2. Methods of Treating Chronic Kidney Disease and Symptoms Thereof

Disclosed herein are methods for treating a subject having, suspected of having, chronic kidney disease or a symptom and/or clinical manifestation thereof by treating, alleviating or reducing albuminuria, and/or reducing kidney cholesterol content, and/or improving renal clearance of cholesterol, and/or treating, alleviating or reducing inflammation in the kidney. In some embodiments, they symptom and/or clinical presentation of chronic kidney disease may include increased albumin in urine and/or decreased glomerular filtration rate.

In some cases, treating a subject as described herein treats, alleviates and/or reduces albuminuria. Impaired reverse cholesterol transport is observed in prevalent (e.g., diabetic kidney disease) and less prevalent (e.g., focal segmental glomerulosclerosis, and Alport syndrome) chronic kidney diseases. Downregulation of ABCA1, which is a major regulator of cellular cholesterol homeostasis by mediating cholesterol transport out of cells, is observed in chronic kidney diseases. Impaired cholesterol homeostasis in the kidney can induce cytotoxicity and secretion of inflammatory cytokines (e.g., TNF), which can lead to kidney damage and albuminuria. Therefore, treating a subject can alleviate and/or reduce such consequences by improving reverse cholesterol transport process in the kidney.

In some instances, treating a subject can alleviate and/or reduce albuminuria at least by 10% or greater (e.g., at least about 15%, at least about 20%, at least about 25%, at least about 30%, at least about 35%, at least about 40%, at least about 45%, at least about 50%, or greater).

In some cases, treating a subject as described herein reduces kidney cholesterol content in the subject. In some cases, the cholesterol content (e.g., free cholesterol) is reduced by at least about 10% or greater (e.g., at least about 15%, at least about 20%, at least about 25%, at least about 30%, at least about 35%, at least about 40%, at least about 45%, at least about 50%, or greater) relative to the cholesterol content prior to treatment with gamma cyclodextrin oligomers.

In some cases, treating a subject as described herein improves renal clearance of cholesterol (e.g., free cholesterol) increased by at least 10% or greater (e.g., at least about 15%, at least about 20%, at least about 25%, at least about 30%, at least about 35%, at least about 40%, at least about 45%, at least about 50%, or greater) relative to renal clearance prior to the treatment.

In some cases, treating a subject as described herein treats, alleviates and/or reduces inflammation (e.g., as measured by cytokine protein, RNA levels, inflammation-targeted imaging modalities) at least by 10% or greater (e.g., at least about 15%, at least about 20%, at least about 25%, at least about 30%, at least about 35%, at least about 40%, at least about 45%, at least about 50%, or greater).

In some cases, reducing cholesterol content, improving renal clearance cholesterol, and/or reducing inflammation in the subject alleviates or reduces the severity or symptoms of chronic kidney disease in the subject. In some cases, the treatment reduces severity or a symptom of chronic kidney disease in the subject or reduces its complications including, but not limited to, heart disease, high blood pressure, anemia, bone weakness, metabolic acidosis and electrolyte disorders, uremic symptoms, hyperkalemia, gout, or fluid retention.

In some instances, treating a subject as described herein reduces the need or dosage of other agents used for the treatment chronic kidney disease to the subject. In some instances, the agents used for the treatment of chronic kidney disease include, but not limited to, ACE inhibitors (e.g., captopril, enalapril, fosinopril, lisinopril, ramipril), ARBs (e.g., azilsartan, eprosartan, irbesartan, losartan, olmesartan, valsartan), CIs (e.g., cyclosporine, tacrolimus), and steroids (e.g., methylprednisolone, prednisone).

In some instances, treating the subject herein can eliminate the need of the treatment with ACE inhibitors, ARBs, CIs, and steroids.

In some instances, treating the subject as described herein can reduce the dosage (e.g., size, amount, frequency, etc.) of ACE inhibitors, ARBs, CIs, and steroids at least 5%, at least 10%, at least 15%, at least 20%, at least 25%, at least 30%, at least 40%, at least 50%, at least 60%, at least 70%, at least 80%, at least 90%, or greater.

In some instances, treating the subject as described herein can reduce the amount of ACE inhibitors, ARBs, Cis, and steroids per treatment at least 5% or greater, at least 10%, at least 15%, at least 20%, at least 25%, at least about 30%, at least 40%, at least 50%, at least 60%, at least 70%, at least 80%, at least 90%, or greater.

In some instances, treating the subject as described herein can reduce the frequency of ACE inhibitors, ARBs, Cis, and steroids per treatment at least 5%, at least 10%, at least 15%, at least 20%, at least 25%, at least 30%, at least 40%, at least 50%, at least 60%, at least 70%, at least 80%, at least 90%, or greater.

In certain instances, treating the subject as described herein maintains the effect of the treatment with ACE inhibitors, ARBs, Cis, or steroids to the subject at least 50%, at least 60%, at least 70%, at least 80%, at least 90%, or even increases the effect at least 5%, at least 10%, at least 20%, at least 30%, at least 40%, or at least 50%.

In certain instances, treating the subject as described herein can decrease the frequency of renal replacement therapy (e.g., hemodialysis, peritoneal dialysis, hemofiltration, and/or hemodiafiltration) treatment to the subject at least 5%, at least 10%, at least 20%, at least 30%, at least 40%, at least 50%, at least 60%, at least 70%, at least 80%, at least 90%, or greater, from example, from three times a week to twice a week, from three times a week to once a week, from three times a week to once two weeks, from three times a week to once a month, from twice a week to once a week, from twice a week to once two weeks, from twice a week to once a month.

In certain instances, treating the subject as described herein can delay the initiation of renal replacement therapy at least 6 months, 7 months, 8 months, 9 months, 10 months, 11 months, 12 months, or greater. In certain instances, treating the subject as described herein can delay kidney transplant in the subject at least 6 months, 7 months, 8 months, 9 months, 10 months, 11 months, 12 months, or greater.

In various aspects, the methods involve administering gamma-cyclodextrin oligomer to a subject. Cyclodextrins are cyclic oligosaccharides that have shown to form complexes with hydrophobic molecules including cholesterol due to their unique structure. They are composed of glucose subunits linked by $\alpha$-1,4 glycosidic bonds. Depending on the number of glucose units, they are classified into alpha-cyclodextrin of six glucoses, beta-cyclodextrin of seven glucoses, and gamma-cyclodextrin of eight glucoses. The native, or parent, cyclodextrins have poor water solubility and highly cytotoxic. Therefore, some chemically modified cyclodextrin have been developed where the hydroxyl groups are replaced, or substituted, with other chemical functional groups to make them water soluble and less cytotoxic. One of its derivatives, hydroxypropyl-beta-cyclodextrin, is in clinical trials for the treatment of varying cholesterol-driven diseases including Niemann-Pick Type C, and Alzheimer's disease. Most commercial HPBCDs have an average of between 4 and 9 hydroxypropyl groups. HPBCD can be selected from VTS-270/adrabetadex, Trappsol® Cyclo™, Kleptose® HP Parenteral Grade, Kleptose® HPB Parenteral Grade, Kleptose® HPB-LB Parenteral Grade, Cavitron® W7 HP5 Pharma cyclodextrin, Cavitron® W7 HP7 Pharma cyclodextrin. However, hydroxypropyl-beta-cyclodextrin can cause disruption of plasma membrane via cholesterol extraction thereof, which can lead to its dose-limiting side effect, ototoxicity, in patients. Furthermore, hydroxypropyl-beta-cyclodextrin and other cyclodextrins are known to cause vacuolation of kidney tubular cells, and even hematuria (e.g., blood in urine), implying its potential toxicity in the kidney.

In various aspects, the methods provided herein involve administering gamma-cyclodextrin oligomer to a subject (e.g., human, non-human animals), in need thereof (e.g., having increased albuminuria, decreased glomerular filtration rate). In some cases, the subject is suspected of having, or is at risk of developing chronic kidney disease.

In some embodiments, the average molecular weight of the gamma-cyclodextrin oligomer is between 2.5 kDa and 20 kDa. In some embodiments, the lower limit of the average molecular weight may be 2.0 kDa, 2.1 kDa, 2.2 kDa, 2.3 kDa, 2.4 kDa, 2.6 kDa, 2.7 kDa, 2.8 kDa, 2.9 kDa, 3.0 kDa, 3.1 kDa, 3.2 kDa, 3.3 kDa, 3.4 kDa, 3.5 kDa, 3.6 kDa, 3.7 kDa, 3.8 kDa, 3.9 kDa, 4.0 kDa, 4.1 kDa, 4.2 kDa, 4.3 kDa, 4.4 kDa, 4.5 kDa, 4.6 kDa, 4.7 kDa, 4.8 kDa, 4.9 kDa, or 5.0 kDa. In some embodiment, the upper limit of the average molecular weight may be 17.5 kDa, 17.6 kDa, 17.7 kDa, 17.8 kDa, 17.9 kDa, 18.0 kDa, 18.1 kDa, 18.2 kDa, 18.3 kDa, 18.4 kDa, 18.5 kDa, 18.6 kDa, 18.7 kDa, 18.8 kDa, 18.9 kDa, 19.0 kDa, 19.1 kDa, 19.2 kDa, 19.3 kDa, 19.4 kDa, 19.5 kDa, 19.6 kDa, 19.7 kDa, 19.8 kDa, 19.9 kDa, 20.1 kDa, 20.2 kDa, 20.3 kDa, 20.4 kDa, 20.5 kDa, 20.6 kDa, 20.7 kDa, 20.8 kDa, 20.9 kDa, 21.0 kDa, 21.1 kDa, 22.2 kDa, 22.3 kDa, 22.4 kDa, 22.5 kDa, 22.6 kDa, 22.7 kDa, 22.8 kDa, 22.9 kDa, 23.0 kDa, 23.1 kDa, 23.2 kDa, 23.3 kDa, 23.4 kDa, 23.5 kDa, 23.6 kDa, 23.7 kDa, 23.8 kDa, 23.9 kDa, 24.0 kDa, 24.1 kDa, 24.2 kDa, 24.3 kDa, 24.4 kDa, 24.5 kDa, 24.6 kDa, 24.7 kDa, 24.8 kDa, 24.9 kDa, 25.0 kDa, 25.1 kDa, 25.2 kDa, 25.3 kDa, 25.4 kDa, 25.5 kDa, 25.6 kDa, 25.7 kDa, 25.8 kDa, 25.9 kDa, or 26.0 kDa.

In some embodiments, the average molecular weight of the gamma-cyclodextrin oligomer is 2.5 kDa to 20 kDa, 2.5 kDa to 19.9 kDa, 2.5 kDa to 19.8 kDa, 2.5 kDa to 19.7 kDa, 2.5 kDa to 19.6 kDa, 2.5 kDa to 19.5 kDa, 2.5 kDa to 19.4 kDa, 3.0 kDa to 20 kDa, 3.0 kDa to 19.9 kDa, 3.0 kDa to 19.8 kDa, 3.0 kDa to 19.7 kDa, 3.0 kDa to 19.6 kDa, 3.0 kDa to 19.5 kDa, 3.0 kDa to 19.4 kDa, 3.5 kDa to 20 kDa, 3.5 kDa to 19.9 kDa, 3.5 kDa to 19.8 kDa, 3.5 kDa to 19.7 kDa, 3.5 kDa to 19.6 kDa, 3.5 kDa to 19.5 kDa, 3.5 kDa to 19.4 kDa, 3.6 kDa to 20 kDa, 3.6 kDa to 19.9 kDa, 3.6 kDa to 19.8 kDa, 3.6 kDa to 19.7 kDa, 3.6 kDa to 19.6 kDa, 3.6 kDa to 19.5 kDa, 3.6 kDa to 19.4 kDa, 3.7 kDa to 20 kDa, 3.7 kDa to 19.9 kDa, 3.7 kDa to 19.8 kDa, 3.7 kDa to 19.7 kDa, 3.7 kDa to 19.6 kDa, 3.7 kDa to 19.5 kDa, 3.7 kDa to 19.4 kDa, 3.8 kDa to 20 kDa, 3.8 kDa to 19.9 kDa, 3.8 kDa to 19.8 kDa, 3.8 kDa to 19.7 kDa, 3.8 kDa to 19.6 kDa, 3.8 kDa to 19.5 kDa, 3.8 kDa to 19.4 kDa, 3.9 kDa to 20 kDa, 3.9 kDa to 19.9 kDa, 3.9 kDa to 19.8 kDa, 3.9 kDa to 19.7 kDa, 3.9 kDa to 19.6 kDa, 3.9 kDa to 19.5 kDa, 3.9 kDa to 19.4 kDa, 4.0 kDa to 20 kDa, 4.0 kDa to 19.9 kDa, 4.0 kDa to 19.8 kDa, 4.0 kDa to 19.7 kDa, 4.0 kDa to 19.6 kDa, 4.0 kDa to 19.5 kDa, 4.0 kDa to 19.4 kDa, 4.1 kDa to 20 kDa, 4.1 kDa to 19.9 kDa, 4.1 kDa to 19.8 kDa, 4.1 kDa to 19.7 kDa, 4.1 kDa to 19.6 kDa, 4.1 kDa to 19.5 kDa, or 4.1 kDa to 19.4 kDa.

In some embodiments, the average molecular weight of the gamma-cyclodextrin oligomer is 6.0 kDa to 10 kDa, 6.0 kDa to 9.5 kDa, 6.0 kDa to 9.0 kDa, 6.0 kDa to 8.5 kDa, 6.0 kDa to 8.4 kDa, 6.0 kDa to 8.3 kDa, 6.5 kDa to 10 kDa, 6.5 kDa to 9.5 kDa, 6.5 kDa to 9.0 kDa, 6.5 kDa to 8.5 kDa, 6.5 kDa to 8.4 kDa, 6.5 kDa to 8.3 kDa, 7.0 kDa to 10 kDa, 7.0 kDa to 9.5 kDa, 7.0 kDa to 9.0 kDa, 7.0 kDa to 8.5 kDa, 7.0 kDa to 8.4 kDa, 7.0 kDa to 8.3 kDa, 7.5 kDa to 10 kDa, 7.5 kDa to 9.5 kDa, 7.5 kDa to 9.0 kDa, 7.5 kDa to 8.5 kDa, 7.5 kDa to 8.4 kDa, 7.5 kDa to 8.3 kDa, 7.7 kDa to 10 kDa, 7.7 kDa to 9.5 kDa, 7.7 kDa to 9.0 kDa, 7.7 kDa to 8.5 kDa, 7.7 kDa to 8.4 kDa, 7.7 kDa to 8.3 kDa, 7.9 kDa to 10 kDa, 7.9 kDa to 9.5 kDa, 7.9 kDa to 9.0 kDa, 7.9 kDa to 8.5 kDa, 7.9 kDa to 8.4 kDa, 7.9 kDa to 8.3 kDa, 8.0 kDa to 10 kDa, 8.0 kDa to 9.5 kDa, 8.0 kDa to 9.0 kDa, 8.0 kDa to 8.5 kDa, 8.0 kDa to 8.4 kDa, 8.0 kDa to 8.3 kDa, 8.1 kDa to 10 kDa, 8.1 kDa to 9.5 kDa, 8.1 kDa to 9.0 kDa, 8.1 kDa to 8.5 kDa, 8.1 kDa to 8.4 kDa, 8.1 kDa to 8.3 kDa, 8.2 kDa to 10 kDa, 8.2 kDa to 9.5 kDa, 8.2 kDa to 9.0 kDa, 8.2 kDa to 8.5 kDa, 8.2 kDa to 8.4 kDa, 8.2 kDa to 8.3 kDa, 8.3 kDa to 10 kDa, 8.3 kDa to 9.5 kDa, 8.3 kDa to 9.0 kDa, 8.3 kDa to 8.5 kDa, or 8.3 kDa to 8.4 kDa. When the average molecular weight of the gamma-cyclodextrin oligomer is out of these ranges, its effect on increasing the levels of ABCA1 may decrease, anti-inflammatory effects may decrease, excreting cholesterol from the body may decrease, and its effect on reducing the level of albuminuria may decrease.

The gamma-cyclodextrin oligomer refers to a polymer formed of at least two gamma-cyclodextrin monomers that are linked by a covalent bond, and, for example, a bifunctional cross-linker such as epichlorohydrin may be used for the cross-linking of the monomers but embodiments are not limited thereto.

In some aspects, the gamma-cyclodextrin oligomer is a molecule comprising at least 2 and at most 10 gamma cyclodextrin monomers. In one aspect, the gamma-cyclodextrin oligomer species can comprise 2 gamma-cyclodextrin monomers, 3 gamma-cyclodextrin monomers, 4 gamma-cyclodextrin monomers, 5 gamma-cyclodextrin monomers, 6 gamma-cyclodextrin monomers, 7 gamma-cyclodextrin monomers, 8 gamma-cyclodextrin monomers, 9 gamma-cyclodextrin monomers, or 10 gamma-cyclodextrin monomers.

In one aspect, provided herein are gamma-cyclodextrin oligomer compositions for the treatment of chronic kidney disease. In certain embodiments, the gamma-cyclodextrin oligomer composition of the present disclosure is a mixture of gamma-cyclodextrin oligomer species. In certain embodiments, the mixture of gamma-cyclodextrin oligomer species comprises a mixture of gamma-cyclodextrin oligomers with at least 2 and at most 10 gamma-cyclodextrin monomers. In some embodiments, the gamma-cyclodextrin oligomer composition comprises a mixture of 2, 3, 4, 5, 6, 7, or 8 gamma-cyclodextrin oligomer species.

In some aspects, the gamma-cyclodextrin monomer is gamma-cyclodextrin or its derivatives. In some aspects, the derivative may be induced by replacing at least one hydrogen in an unsubstituted mother group with another atom or a functional group. The functional group may be substituted with at least one substituent selected from halides, C1-C40 alkyl groups, C2-C40 alkenyl groups, C2-C40 alkynyl groups, C3-C40 cycloalkyl groups, C3-C40 cycloalkenyl groups, and C7-C40 aryl groups. For example, the hydrogen can be replaced with C1-C10 linear or branched alkyl, hydroxy C1-C10 linear or branched alkyl, sulfobutylether C1-C10 linear or branched alkyl, or carboxy C1-C10 linear or branched alkyl; particularly, C1-C5 linear or branched alkyl, hydroxy C1-C5 linear or branched alkyl, sulfobutylether C1-C5 linear or branched alkyl, or carboxy C1-C5 linear or branched alkyl; or more particularly, methyl, hydroxypropyl, sulfobutylether, or carboxy methyl, but embodiments are not limited thereto.

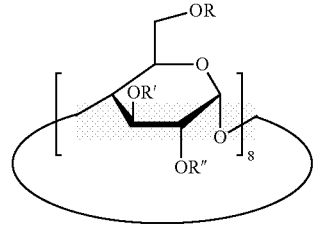

[Formula 1]

In some aspects, the gamma-cyclodextrin monomer is represented by Formula 1. R, R' and R" bonded to hydroxyl groups of C2, C3, and C6 of Formula 1 may be, for example, hydrogen, C1-C10 linear or branched alkyl, hydroxy C1-C10 linear or branched alkyl, sulfobutylether C1-C10 linear or branched alkyl, or carboxy C1-C10 linear or branched alkyl; particularly, may be hydrogen, C1-C5 linear or branched alkyl, hydroxy C1-C5 linear or branched alkyl, sulfobutylether C1-C5 linear or branched alkyl, or carboxy C1-C5 linear or branched alkyl; or more particularly, may be hydrogen, methyl, hydroxypropyl, sulfobutylether, or carboxy methyl, but embodiments are not limited thereto.

In the gamma-cyclodextrin derivative of Formula 1, the number of the substituted hydroxy groups may be, for example, 1 to 24, 1 to 18, 1 to 12, 2 to 24, 2 to 18, 3 to 24, 3 to 12, 4 to 6, or about 5, but embodiments are not limited thereto.

When the substituted hydrogen per one glucose is shown as a molar substitution, the molar substitution of the gamma-cyclodextrin derivative may be between 0.2 and 0.9. In some embodiments, the molar substitution value may be between, for example, about 0.2 to about 0.9, about 0.3 to about 0.9, about 0.4 to about 0.9, about 0.5 to about 0.9, about 0.6 to about 0.9, about 0.7 to about 0.9, about 0.2 to about 0.8, about 0.3 to about 0.8, about 0.4 to about 0.8, about 0.5 to about 0.8, about 0.6 to about 0.8, about 0.2 to about 0.7, about 0.3 to about 0.7, about 0.4 to about 0.7, about 0.5 to about 0.7, about 0.2 to about 0.6, about 0.3 to about 0.6, about 0.4 to about 0.6. In some embodiments, the derivative is hydroxypropyl-gamma-cyclodextrin with a molar substitution value between 0.2 and 0.9.

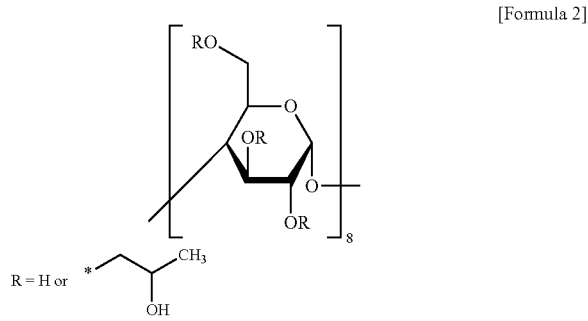

[Formula 2]

In some aspects, the gamma-cyclodextrin monomer is hydroxypropyl-gamma-cyclodextrin by Formula 2 having a molar substitution in a range of about 0.5 to about 0.75.

In some aspects, the gamma-cyclodextrin oligomer is chemically modified by replacing a part of the structure (e.g., hydrogen) with another atom or a functional group selected from halides, C1-C40 alkyl groups, C2-C40 alkenyl groups, C2-C40 alkynyl groups, C3-C40 cycloalkyl groups, C3-C40 cycloalkenyl groups, and C7-C40 aryl groups. For example, the hydrogen can be replaced with C1-C10 linear or branched alkyl, hydroxy C1-C10 linear or branched alkyl, sulfobutylether C1-C10 linear or branched alkyl, or carboxy C1-C10 linear or branched alkyl; particularly, C1-C5 linear or branched alkyl, hydroxy C1-C5 linear or branched alkyl, sulfobutylether C1-C5 linear or branched alkyl, or carboxy C1-C5 linear or branched alkyl; or more particularly, methyl, hydroxypropyl, sulfobutylether, or carboxy methyl, but embodiments are not limited thereto.

In some aspects, the gamma cyclodextrin oligomer is formed using bifunctional crosslinking agents (e.g., bifunctional alkylating agent). In a particular embodiment, the bifunctional crosslinking agent is epichlorohydrin.

In some cases, gamma-cyclodextrin oligomer comprises 10% (w/w) or less of gamma-cyclodextrin monomers. In some cases, gamma-cyclodextrin oligomer comprises less than about 10% (w/w), less than about 9% (w/w), less than about 8% (w/w), less than about 7% (w/w), less than about 6% (w/w), less than about 5% (w/w), less than about 4% (w/w), less than about 3% (w/w), less than about 2% (w/w), less than about 1% (w/w), less than about 0.5% (w/w), less than about 0.4% (w/w), less than about 0.3% (w/w), less than about 0.2% (w/w), less than about 0.1% (w/w), less than about 0.05% (w/w), or less than about 0.01% of gamma-cyclodextrin monomers.

In various aspects, a therapeutically effective amount of gamma-cyclodextrin oligomer is administered to the subject. In some aspects, administration of a therapeutically effective amount of gamma-cyclodextrin oligomer increases expression of ABCA1 gene or protein in the kidney at least 5%, at least 10%, at least 15%, at least 20%, at least 30%, at least 40%, at least 50%, at least 60%, at least 70%, at least 80%, at least 90%, at least 100%, at least 200% in the subject as compared to prior to treatment. In some aspects, administration of a therapeutically effective amount of gamma-cyclodextrin oligomer increases expression of Niemann-Pick C1 (NPC1) gene or protein in the kidney at least 5%, at least 10%, at least 15%, at least 20%, at least 30%, at least 40%, at least 50%, at least 60%, at least 70%, at least 80%, at least 90%, at least 100%, or at least 200%. In some aspects, administration of a therapeutically effective amount of gamma-cyclodextrin oligomer decreases expression of low-density lipoprotein receptor (LDLR) gene or protein in the kidney at least 5%, at least 10%, at least 15%, at least 20%, at least 30%, at least 40%, at least 50%, at least 60%, at least 70%, at least 80%, at least 90%, at least 100%, or at least 200%. In some aspects, administration of a therapeutically effective amount of gamma-cyclodextrin oligomer reduces kidney fibrosis at least 5%, at least 10%, at least 15%, at least 20%, at least 30%, at least 40%, at least 50%, at least 60%, at least 70%, at least 80%, at least 90%, or at least 100%. In some aspects, administration of a therapeutically effective amount of gamma-cyclodextrin oligomer improves glomerular filtration ratio at least 5%, at least 10%, at least 15%, at least 20%, at least 30%, at least 40%, at least 50%, at least 60%, at least 70%, at least 80%, at least 90%, at least 100%, or at least 200%.

In some embodiments, the gamma-cyclodextrin oligomer facilitates transport, efflux, and/or clearance of cholesterol (e.g., by increasing expression of ABCA1 gene or protein) in the kidney or other organs including, but not limited to, the liver, blood vessel, heart, spleen, lung, eyes, brain, or skin. In some embodiments, the gamma-cyclodextrin oligomer reduces cholesterol, and/or improves clearance of cholesterol, thereby alleviating or reducing inflammation in the other organs. In some embodiments, alleviating or reducing inflammation in the other organs affects alleviating or reducing inflammation in the kidney. In some embodiments, alleviating or reducing inflammation in the kidney affects alleviating or reducing inflammation in the other organs.

In some aspects, the therapeutically effective amount of gamma-cyclodextrin oligomer is an amount enough to achieve the therapeutic effect described herein. In some aspects, the therapeutically effective amount is at least about 20 mg/kg, at least 30 mg/kg, at least 40 mg/kg, at least about 50 mg/kg, at least about 60 mg/kg, at least 70 mg/kg, at least 80 mg/kg, at least 90 mg/kg, least about 100 mg/kg, at least about 200 mg/kg, at least about 300 mg/kg, at least about 400 mg/kg, at least about 500 mg/kg, at least about 600 mg/kg, at least about 700 mg/kg, at least about 800 mg/kg, at least about 900 mg/kg, at least about 1000 mg/kg, at least about 1100 mg/kg, at least about 1200 mg/kg, at least about 1300 mg/kg, at least about 1400 mg/kg, at least about 1500 mg/kg, at least about 1600 mg/kg, at least about 1700 mg/kg, at least about 1800 mg/kg, at least about 1900 mg/kg, at least about 2000 mg/kg, at least about 2500 mg/kg, at least about 3000 mg/kg, at least about 3500 mg/kg, or at least about 4000 mg/kg. In some aspects the therapeutically effective amount of gamma-cyclodextrin oligomer is at least about 50 mg/kg. In some aspects, the therapeutically effective amount of gamma-cyclodextrin oligomer is at least about 100 mg/kg. In some aspects, the therapeutically effective amount of gamma-cyclodextrin oligomer is at least about 250 mg/kg. In some aspects, the therapeutically effective amount of gamma-cyclodextrin oligomer is at least about 500 mg/kg. In some aspects, the therapeutically effective amount of gamma-cyclodextrin oligomer is at least about 1000 mg/kg. In some aspects, the therapeutically effective amount of gamma-cyclodextrin oligomer is at least about 2000 mg/kg.

In some aspects, the therapeutically effective amount of gamma-cyclodextrin oligomer is an amount enough to achieve the therapeutic effect described herein. In some aspects, the therapeutically effective amount is from about 20 mg/kg to about 2000 mg/kg (e.g., from about 20 mg/kg to about 1000 mg/kg, from about 20 mg/kg to about 1500 mg/kg, from about 50 mg/kg to about 1000 mg/kg, from about 50 mg/kg to 1500 mg/kg, from about 50 mg/kg to about 2000 mg/kg, from about 100 mg/kg to about 1000 mg/kg, from about 100 mg/kg to about 1500 mg/kg, from 100 mg/kg to about 2000 mg/kg, from about 500 mg/kg to about 1000 mg/kg, from about 500 mg/kg to about 1500 mg/kg, from about 500 mg/kg to about 2000 mg/kg, from about 1000 mg/kg to about 1500 mg/kg, from about 1500 mg/kg to 2000 mg/kg). In some aspects, the therapeutically effective amount of gamma-cyclodextrin oligomer is from about 100 mg/kg to about 1000 mg/kg. In some aspects, the therapeutically effective amount of gamma-cyclodextrin oligomer is from about 500 mg/kg to about 2000 mg/kg.

In some aspects, the therapeutically effective amount of gamma-cyclodextrin oligomer is an amount enough to achieve the therapeutic effect described herein. In some aspects, the therapeutically effective amount is at least about 1 g, at least about 2 g, at least about 3 g, at least about 4 g, at least about 5 g, at least about 6 g, at least about 7 g, at least about 8 g, at least about 9 g, at least about 9 g, at least about 10 g, at least about 25 g, at least about 50 g, at least about 75 g, at least about 100 g, at least about 150 g, or at least about 200 g. In some aspects, the therapeutically effective amount of gamma-cyclodextrin oligomer may be from about 1 to about 200 g, from about 1 g to 100 g, from about 1 g to 50 g, from about 5 g to about 200 g, from about 5 g to about 150 g, from about 5 g to about 100 g, from about 5 g to 50 g, from about 10 g to 200 g, from about 10 g to 150 g, from about 10 g to 100 g, from about 10 g to 50 g, from about 50 g to about 200 g, from about 50 g to about 150 g, from about 50 g to about 100 g, from about 100 g to 200 g, from about 100 g to about 150 g, from about 150 g to about 200 g. The total amount of gamma-cyclodextrin oligomer administered (e.g., in a single dose administration, e.g., in a therapeutically effective amount) may depend on a number of factors, including, but not limited to, the subject's disease stage, renal function (e.g., as measured by albuminuria and/or glomerular filtration rate), age, gender, weight, etc.

In some aspects, the therapeutically effective amount of gamma-cyclodextrin oligomer is an amount enough to achieve a whole blood, serum, and/or plasma concentration of gamma-cyclodextrin oligomer enough for achieving the therapeutic effect described herein. In some aspects, the whole blood, serum, and/or plasma concentration is at least about 0.01 mg/ml (e.g., at least ab out 0.05 mg/ml, at least about 0.1 mg/ml, at least about 0.2 mg/ml, at least about 0.3 mg/ml, at least about 0.4 mg/ml, at least about 0.5 mg/ml, at least about 0.6 mg/ml, at least about 0.7 mg/ml, at least about 0.8 mg/ml, at least about 0.9 mg/ml, at least about 1 mg/ml, at least about 1.5 mg/ml, at least about 2.0 mg/ml, at least about 2.5 mg/ml, at least about 5 mg/ml, at least about 6 mg/ml, at least about 7 mg/ml, at least about 8 mg/ml, at least about 9 mg/ml, at least about 10 mg/ml, at least about 15 mg/ml, at least about 20 mg/ml).

The methods disclosed herein may further comprise administering a therapeutically effective amount of gamma-cyclodextrin oligomer to a subject multiple times. The administering comprises administering every day, every 3 days, every 7 days, every 10 days, every 14 days, every 21 days, every 28 days, every 2 months, every 3 months, every 6 months, every 12 months.

In some instances, the treatment of gamma-cyclodextrin oligomer is combined with other agents used for the treatment of chronic kidney disease (e.g., ACE inhibitors, ARBs, CIs, or steroids). In some cases, the gamma-cyclodextrin oligomer is concurrently administered to the subject. In some cases, the gamma-cyclodextrin oligomer is sequentially administered to the subject.

In some cases, the subject may be treated before developing chronic kidney disease. For example, a subject at risk of developing chronic kidney disease (e.g., a subject with elevated albuminuria, a subject with genetic background) may be treated by the methods described herein, for example, to delay the disease progression, e.g., to alleviate or reduce albuminuria, reduce kidney cholesterol, improve renal clearance of cholesterol, and/or alleviate or reduce kidney inflammation.

In some aspects, the methods involve treating a subject with a combination of gamma-cyclodextrin oligomer and an additional therapeutic (e.g., active pharmaceutical ingredients, medical procedure, or surgery).

In some cases, the gamma-cyclodextrin oligomer and the additional therapeutic are administered to the subject at or near the same time (e.g., in a single formulation, or as separate formulations). In some cases, the gamma-cyclodextrin oligomer and the additional therapeutic are administered at different times (e.g., in separate formulations). In some cases, the additional therapeutic is administered prior to administration of gamma-cyclodextrin oligomer. In some cases, the additional therapeutic is administered after administration of gamma-cyclodextrin oligomer.

In some aspects, the subject may have previously been undergoing treatment with an additional therapeutic prior to administration of gamma-cyclodextrin oligomers. In some cases, the treatment with the additional therapeutic may be ineffective or may have limited efficacy. In such cases, subjects treated with gamma-cyclodextrin oligomer may exhibit a greater therapeutic benefit than administration of the additional treatment alone.

In some cases, subjects treated with both gamma-cyclodextrin oligomer and an additional therapeutic may exhibit a therapeutic benefit greater than the therapeutic benefit exhibited by treatment with either the additional therapeutic or the gamma-cyclodextrin oligomer alone. In some cases, treatment with both the additional therapeutic and gamma-cyclodextrin oligomer has a synergistic effect, such that the interaction between the additional therapeutic and gamma-cyclodextrin oligomer causes the total effect of the therapeutics to be greater than the sum of the individual effects of each therapeutic. In some cases, treatment with both the additional therapeutic and gamma-cyclodextrin oligomer has an additive effect.

3. Pharmaceutical Composition

In one aspect, the disclosure provides pharmaceutical compositions comprising the gamma-cyclodextrin oligomer for the treatment of chronic kidney disease and/or one or more symptoms and/or clinical manifestations of chronic kidney disease, in a subject. In some embodiments, the subject is a human patient.

The pharmaceutical composition may further include a pharmaceutical additive selected from the group consisting of a diluent, a binder, a disintegrant, a lubricant, an enhancer, and any combination thereof other than the gamma-cyclodextrin polymer. Also, the pharmaceutical composition may be formulated into injections such as aqueous solutions, suspensions, emulsions, etc., pills, capsules, granules or tablets, with the aid of a diluent, a dispersant, a surfactant, a binder, and/or a lubricant. Also, the pharmaceutical composition may further include a pharmaceutically acceptable carrier, i.e., saline, sterile water, Ringer's solution, buffered saline, cyclodextrin, a dextrose solution, a maltodextrin solution, glycerol, ethanol, liposome, or a mixture of one or more thereof, and if necessary, other common additive such as an antioxidant, a buffer, etc. Moreover, the pharmaceutical composition may be formulated according to respective components using an appropriate method known in the art or a method disclosed in Remington's Pharmaceutical Science (Mack Publishing Company, Easton PA).

The diluent, which may be used to increase quantity, may be selected from the group consisting of mannitol, lactose, starch, microcrystalline cellulose, Ludipress®, calcium dihydrogen phosphate, and any combinations thereof, but embodiments are not limited thereto.

The binder may be selected from the group consisting of povidone, hydroxypropyl cellulose, hydroxypropyl methyl cellulose, polyvinyl alcohol, sodium carboxymethyl cellulose, and any combinations thereof, but embodiments are not limited thereto.

The disintegrant may be selected from the group consisting of croscarmellose sodium, crospovidone, sodium starch glycolate, and any combinations thereof, but embodiments are not limited thereto.

The lubricant may be selected from the group consisting of stearic acid, metal salts of stearic acid (for example, calcium stearate, or magnesium stearate), talc, colloid silica, sucrose fatty acid ester, hydrogenated vegetable oil, wax, glyceryl fatty acid esters, glycerol dibehenate, and any combinations thereof, but embodiments are not limited thereto.

The enhancer may be hyaluronidase (e.g., hyaluronidase 1-4, PH20, or HYALP1).

In some embodiments, the pharmaceutical composition comprises at least about 1 g, at least about 2 g, at least about 3 g, at least about 4 g, at least about 5 g, at least about 6 g, at least about 7 g, at least about 8 g, at least about 9 g, at least about 9 g, at least about 10 g, at least about 25 g, at least about 50 g, at least about 75 g, at least about 100 g, at least about 150 g, or at least about 200 g of gamma-cyclodextrin oligomer. In some aspects, the pharmaceutical composition comprises from about 1 to about 200 g, from about 1 g to 100 g, from about 1 g to 50 g, from about 5 g to about 200 g, from about 5 g to about 150 g, from about 5 g to about 100 g, from about 5 g to 50 g, from about 10 g to 200 g, from about 10 g to 150 g, from about 10 g to 100 g, from about 10 g to 50 g, from about 50 g to about 200 g, from about 50 g to about 150 g, from about 50 g to about 100 g, from about 100 g to 200 g, from about 100 g to about 150 g, or from about 150 g to about 200 g of gamma-cyclodextrin oligomer.

In some embodiments, the pharmaceutical compositions of the present disclosure further comprise one or more pharmaceutically acceptable excipients. In some embodiments, the one or more pharmaceutically acceptable excipients can be selected from the group comprising a diluent, a buffering agent, a stabilizer, a solubilizing agent, a preservative, an enhancer, or any combination thereof.

In certain embodiments, the pharmaceutical composition may be formulated for administration as a liquid dosage form suitable form suitable for intravenous, intravascular, subcutaneous, intramuscular, intrathecal, depot, and peristaltic pump administration.

In some embodiments, the pharmaceutical composition may be administered by a device (e.g., wearable injection systems).

4. Examples

Example 1. Preparation of Cyclodextrins

For hydroxypropyl-beta-cyclodextrins (HPBCD), those with different molecular weights, or degree of substitution, or molar substitution, were purchased from Sigma Aldrich. HPBCD-A, HPBCD-B, and HPBCD-C have average molecular weights of 1396 Da (Cat #H107), 1460 Da (Cat #332607), and 1540 Da (Cat #389145), respectively.

For gamma cyclodextrin oligomers, gamma cyclodextrin or its derivatives were dissolved in 33% NaOH solution and then an appropriate amount of epichlorohydrin was added to induce oligomerization. After 24 hours, acetone was added to stop the oligomerization reaction and then acetone was removed by decantation. The remaining solution was incubated in the oven at 50° C. for 24 hours. The pH of the solution was adjusted to between 6 and 11 using hydrochloric acid. Salts, cyclodextrin monomers, and small byproducts were removed using dialysis and/or ultrafiltration. Freeze drying was performed to obtain dried form of gamma cyclodextrin oligomers.

Figure 1B:
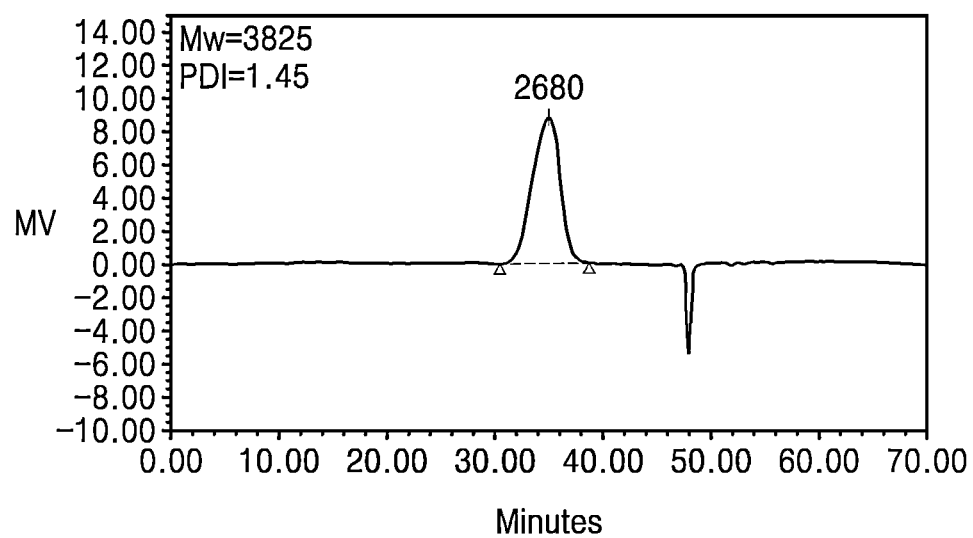
Figure 2A:
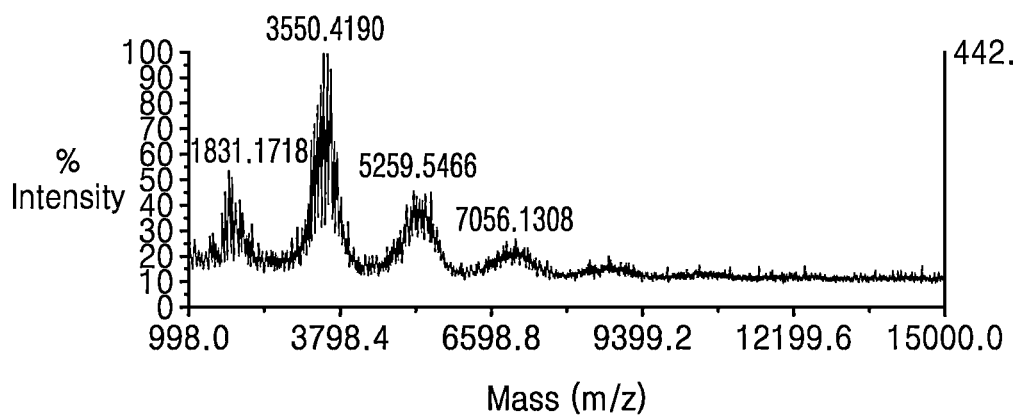
FIG. 2A and FIG. 2B show the matrix-assisted laser desorption ionization time of flight mass spectrometer data confirming the formation of oligomers of hydroxypropyl-gamma-cyclodextrin with average molecular weight of 3.8 kDa (A) and 8.8 kDa (B).
Figure 2B:
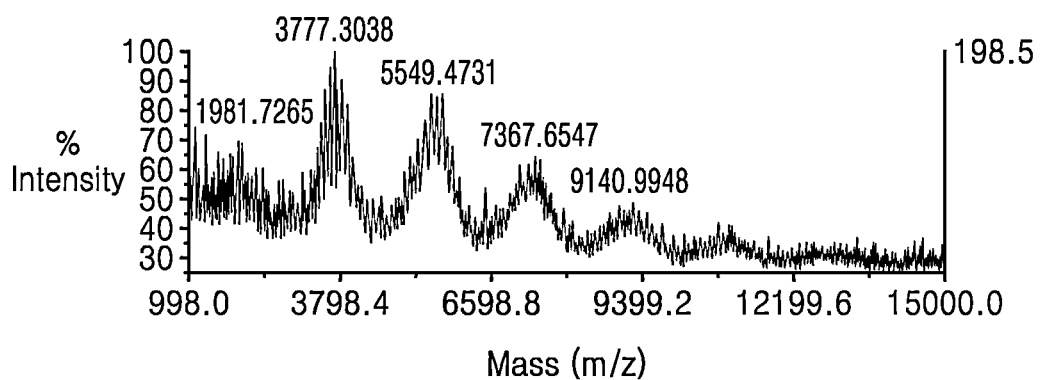

As shown in FIG. 1, the gamma-cyclodextrin oligomer comprising gamma-cyclodextrin monomers (Oligo-GCD) (FIG. 1A) and hydroxypropyl-gamma-cyclodextrin monomers (Oligo-HPGCD) (FIG. 1B) had average molecular weights 4103 Da and 3825 Da, respectively. As shown in FIG. 2, the successful formation of oligomers of gamma-cyclodextrins could be validated through matrix-assisted laser desorption ionization time of flight mass spectrometer.

Example 2. Plasma Membrane Disruption and Cholesterol Metabolism Enhancement by Cyclodextrins 2.1 Plasma Membrane Cholesterol Extraction Assay A macrophage cell line (Raw264.7) was used for the assessment of plasma membrane cholesterol extraction by cyclodextrins. $1\times10^5$ cells were seeded in a 6-well plate and 24 hours later cyclodextrins dissolved in PBS at 20 mg/ml were treated to the fixed cells for 1 hour at 37° C. The supernatant was collected, centrifuged at 14,000 g for 30 minutes to remove cell debris and microvesicles. The amount of extracted cholesterol was quantified using a Cholesterol Quantification Kit (Sigma Aldrich).

Figure 3A:
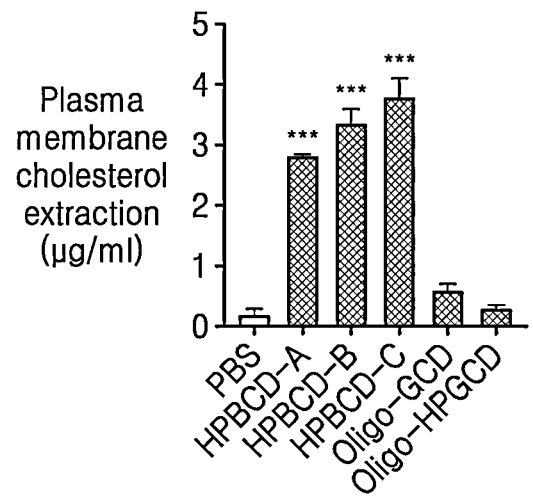
FIG. 3A to FIG. 3F show the effects of gamma-cyclodextrin oligomers (Oligo-GCD, Oligo-HPGCD) and HPBCDs (HPBCD-A, HPBCD-B, HPBCD-C) on plasma membrane disruption through the assessment of plasma membrane cholesterol extraction (A), hemolytic activity (B), and cellular viability (C) of the cyclodextrins, and the effects of the cyclodextrins on cholesterol metabolism modulation through the assessment of their efficacy in cholesterol crystal (CC) dissolution (D), cholesterol efflux (E), and ABCA1 expression (F). Data are mean±SD. ***P<0.001 compared to PBS; One-way ANOVA analysis and Tukey's multiple comparisons test (n=3).

As shown in FIG. 3A, gamma-cyclodextrin oligomers (Oligo-GCD and Oligo-HPGCD) exhibited plasma membrane cholesterol extraction significantly reduced compared to HPBCDs (HPBCD-A, HPBCD-B, HPBCD-C). The results show that gamma-cyclodextrin oligomers have minimal effect on plasma membrane cholesterol extraction and will not hamper the integrity of the plasma membrane.

2.2 Hemolysis Assay

Whole blood from wilt-type C57/BL6 mice was used for assessment of hemolytic activity of cyclodextrins. The whole blood samples (300 µl) were mixed with each cyclodextrin at a concentration of 50 mg/ml and incubated for 1 hour at 37° C. After centrifugation at 3,000 g for 5 minutes, the absorbance at 540 nm of the supernatant was measured.

Figure 3B:
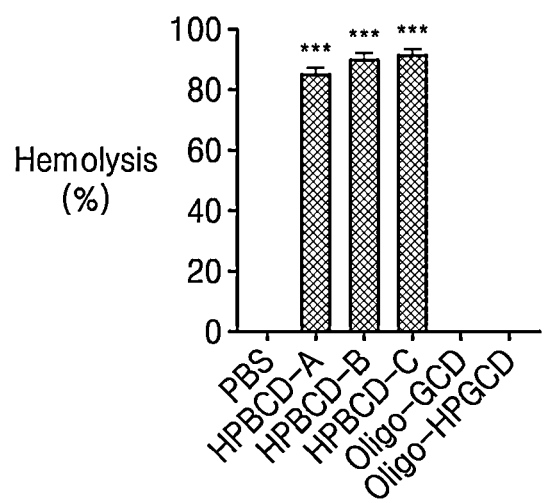

As shown in FIG. 3B, gamma-cyclodextrin oligomers (Oligo-GCD and Oligo-HPGCD) exhibited hemolytic activity significantly reduced compared to HPBCDs (HPBCD-A, HPBCD-B, HPBCD-C). The results demonstrate that gamma-cyclodextrin oligomers do not disrupt the plasma membrane of red blood cells whereas HPBCDs disrupt the plasma membrane and induce hemolysis.

2.3 Cell Viability Assay

The cells were seeded in a 96-well plate at a density of $5 \times 10^4$ cells and 24 hours later cyclodextrin were treated at a concentration of 20 mg/ml for 24 hours at 37° C. CCK-8 agent was added, 10 µl per well. After 3 hours, absorbance at 450 nm was measured to assess cellular viability.

Figure 3C:
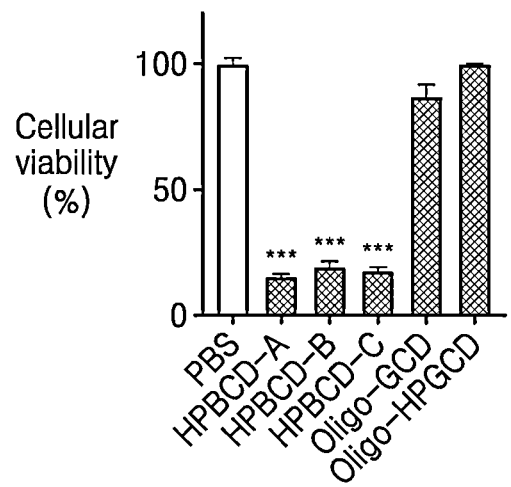

As shown in FIG. 3C, the cells treated with gamma-cyclodextrin oligomers (Oligo-GCD and Oligo-HPGCD) exhibited cell viability significantly higher than those treated with HPBCDs (HPBCD-A, HPBCD-B, HPBCD-C). The results confirm that gamma-cyclodextrin oligomers do not disrupt the plasma membrane of the cells whereas HPBCDs disrupt the plasma membrane and induce cell viability loss.

2.4 Cholesterol Crystal (CC) Dissolution Assay

To prepare cholesterol crystals containing NBD fluorophore-conjugated cholesterol, cholesterol and NBD-cholesterol was dissolved in 1-propanol at a concentration of 2 mg/ml and 0.2 mg/ml, respectively. Then, 1.5 parts water was added to induce crystallization. The solution was then freeze-dried to obtain dry CC. For CC dissolution assay, the dry CC was resuspended in PBS, sonicated for 30 seconds. Then, 20 µM of 5 mM cholesterol was mixed with 300 µl of 20 mg/ml cyclodextrins, which were incubated for 2 hours at 37° C. After centrifugation at 14,000 g for 30 minutes to remove undissolved cholesterol crystals, the supernatant was collected and the fluorescence at 480 nm/520 nm was measured.

Figure 3D:
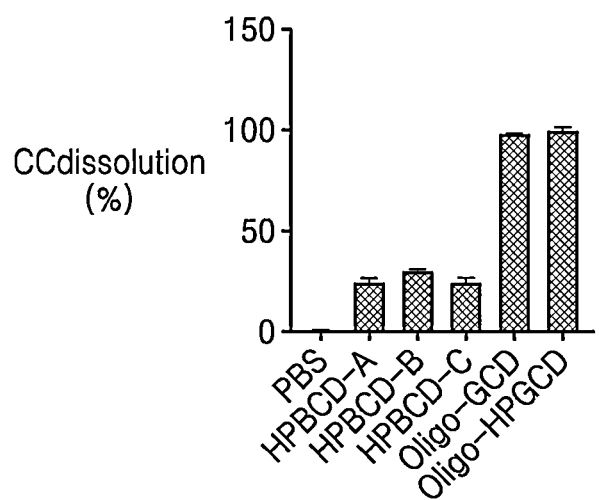

As shown in FIG. 3D, gamma-cyclodextrin oligomers (Oligo-GCD and Oligo-HPGCD)s exhibited superior efficacy in cholesterol crystal dissolution over HPBCDs (HPBCD-A, HPBCD-B, HPBCD-C). The results show that the gamma-cyclodextrin oligomers have more potential to solubilize cholesterol crystals and facilitate their transport and clearance inside and/or outside cells.

2.5 Intracellular Cholesterol and ABCA1 Quantification

The macrophage cell line was seeded in a 96-well plate at a density of $5 \times 10^4$ cells. After 24 hours, the cells were treated with CC containing NBD-cholesterol at a concentration of 50 µM for 3 hours. Then, the cells were washed thoroughly and treated with cyclodextrins at a concentration of 5 mg/ml for 24 hours. Intracellular cholesterol was quantified using flow cytometry. For quantification of ABCA1, the cells were treated with cyclodextrin for 48 hours and then anti-ABCA1 antibodies were treated for flow cytometry analysis.

Figure 3E:
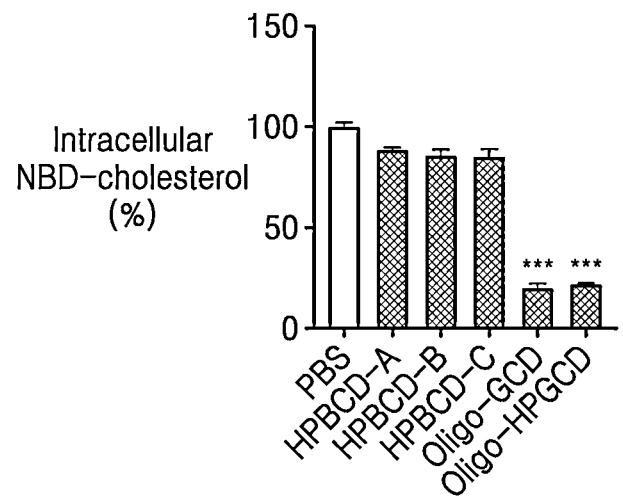
Figure 3F:
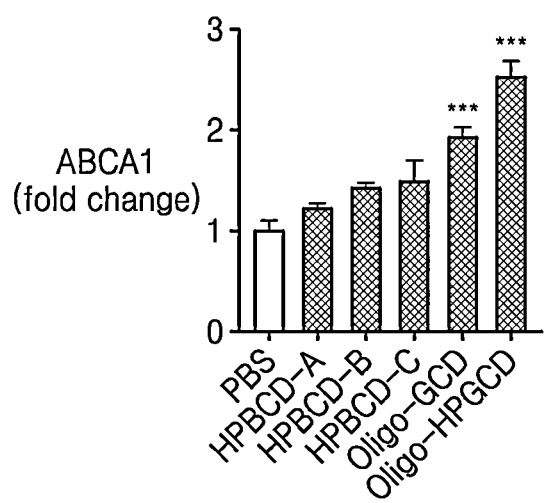

As shown in FIG. 3E, the cells treated with gamma-cyclodextrin oligomers (Oligo-GCD and Oligo-HPGCD) exhibited significantly lower amount of intracellular NBD-cholesterol compared to those treated with HPBCDs (HPBCD-A, HPBCD-B, HPBCD-C). The results show that the gamma-cyclodextrin oligomers have more potential to promote and/or induce cholesterol efflux. Furthermore, as shown in FIG. 3F, the cells treated with gamma-cyclodextrin oligomers exhibited expression of ABCA1 proteins significantly higher than those treated with HPBCDs. The results demonstrate that the gamma-cyclodextrin oligomers can more effectively facilitate cholesterol efflux, in part, by upregulation of ABCA1 proteins.

Example 3. Effects on Cholesterol Efflux in Kidney Cells

Murine mesangial cells derived from the kidney of wild-type C57BL/6 mice were maintained in DMEM, 10% fetal bovine serum (FBS), 100 U/ml penicillin G, 100 µg/ml streptomycin, and 2 mM L-glutamine. The cells were seeded at a density of $10^6$ cells/well one day before treatment with NBD-CC. The cells were treated with 100 µg of NBD-CC per $10^6$ cells for 3 hours and then washed thoroughly twice. Then, cyclodextrins were treated at a concentration of 5 mg/ml. For the assessment of cholesterol efflux and efflux-mediating proteins ABCA1 and ABCG1, flow cytometry was performed.

Figure 4A:
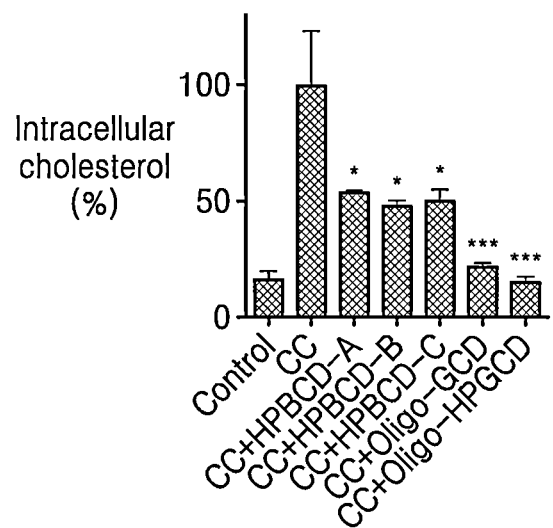
FIG. 4A to FIG. 4C show the effects of gamma-cyclodextrin oligomers and HPBCDs on cholesterol modulation in kidney cells as assessed by intracellular cholesterol content (A), and the expression of ABCA1 (B) and ABCG1 (C). The cells treated with CC containing fluorophore-conjugated cholesterol were treated with the cyclodextrins and flow cytometry was performed. The control group was not treated with CC. The CC group was treated with CC and not treated with cyclodextrins. Data are mean±SD. *P<0.05, P<0.01, *P<0.001, compared to CC; One-way ANOVA analysis and Tukey's multiple comparisons test (n=3).
Figure 4A:
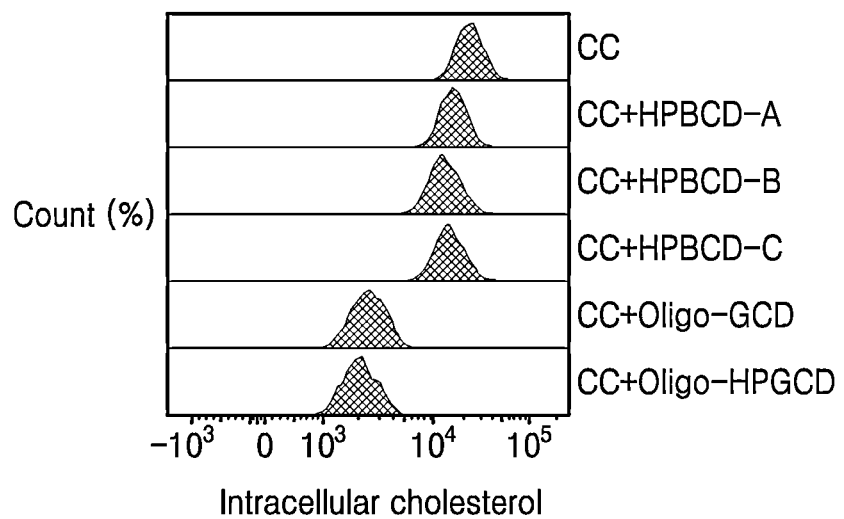
Figure 4B:
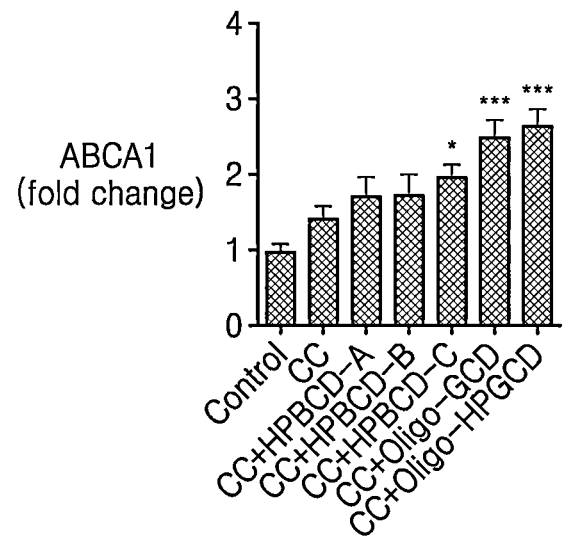
Figure 4C:
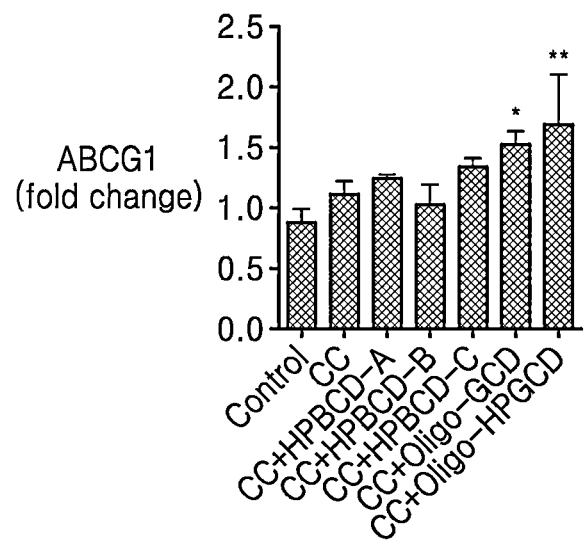

As shown in FIG. 4A, the mesangial cells treated with CC showed very high cellular cholesterol content and treatment with cyclodextrin induced significant reduction in the cholesterol content. Among cyclodextrins, the gamma-cyclodextrin oligomers (Oligo-GCD: 22.5%, Oligo-HPGCD: 15.9%) exhibited superior efficacy in cholesterol efflux over HPBCDs (HPBCD-A: 54.1%, HPBCD-B: 48.2%, HPBCD-C: 50.5%). The results show that the gamma-cyclodextrin oligomers exhibit excellent cholesterol efflux efficacy, which was on average 180% more effective than HPBCDs. As shown in FIG. 4B and C, the cells treated with the gamma-cyclodextrin oligomer showed significant overexpression of ABCA1 and ABCG1 compared to HPBCDs. The results confirm that the gamma-cyclodextrin oligomers effectively modulates the major cholesterol efflux pathways.

Example 4. Effects on Inflammatory Cytokine Secretion in Kidney Cells

Murine mesangial cells derived from the kidney of wild-type C57BL/6 mice were maintained in DMEM, 10% fetal bovine serum (FBS), 100 U/ml penicillin G, 100 µg/ml streptomycin, and 2 mM L-glutamine. The cells were seeded at a density of $10^6$ cells/well one day before treatment with NBD-CC. The cells were treated with 100 µg of NBD-CC per $10^6$ cells for 3 hours and then washed thoroughly twice. Then, cyclodextrins were treated at a concentration of 5 mg/ml. For the assessment of the secretion of inflammatory cytokines tumor necrosis factor-α (TNF-α) and interferon-γ (IFN-γ), the supernatant of the cell culture was collected and used for enzyme-linked immunosorbent assay (ELISA). TNF-α is increased in chronic kidney disease, which is characterized by progressive loss of renal function, renal injury, and hypertension. Dysregulated cholesterol efflux can contribute to the pathogenesis of chronic kidney disease, in part by inducing the secretion of TNF-α. High concentrations of intracellular cholesterol or cholesterol crystal formation can activate NLRP3 inflammasomes, which increases IFN-γ and promotes pro-inflammatory pathways.

Figure 5:
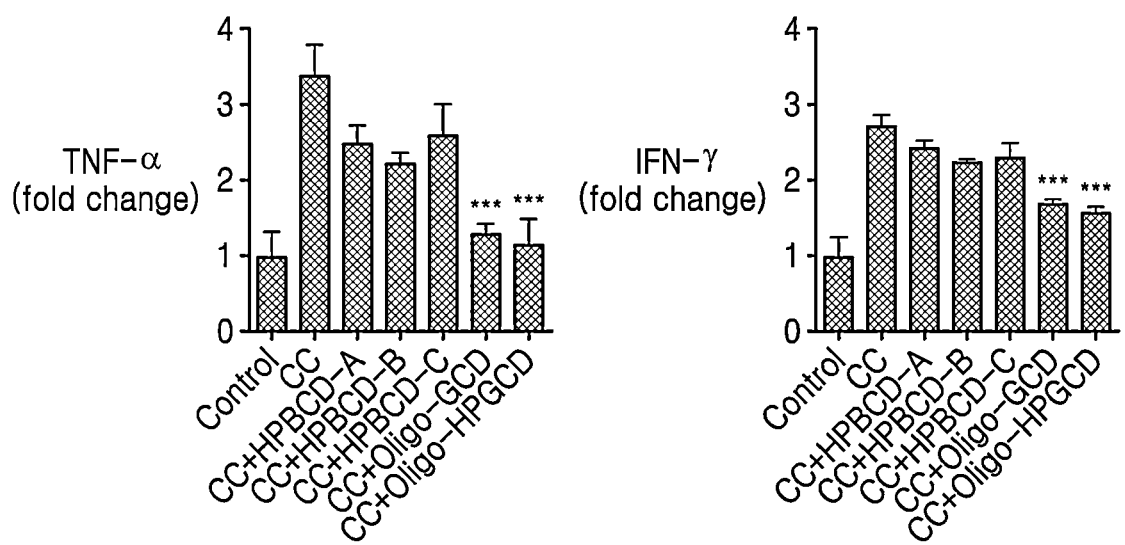
FIG. 5 shows the effects of gamma-cyclodextrin oligomers and HPBCDs on the secretion of pro-inflammatory cytokines in kidney cells as assessed by the secretion of TNF-α and IFN-β using enzyme-linked immunosorbent assay (ELISA). The cells treated with CC were treated with the cyclodextrins and ELISA was performed to measure the inflammatory cytokines in the supernatant. The control group was not treated with CC. The CC group was treated with CC and not treated with cyclodextrins. Data are mean±SD. ***P<0.001 compared to CC; One-way ANOVA analysis and Tukey's multiple comparisons test (n=3).

As shown in FIG. 5, the cells treated with CC resulted in significant increase in the secretion of the inflammatory cytokines. When the cells were treated with cyclodextrin, however, the secretion could be alleviated or reduced. We can see that gamma-cyclodextrin oligomers exhibited superior efficacy in reducing both inflammatory cytokines compared to HPBCDs. The results demonstrate that cholesterol-induced pro-inflammatory signals can be effectively prevented by using gamma-cyclodextrin oligomers.

Example 5. Effects on Renal Clearance of Cholesterol

Figure 6A:
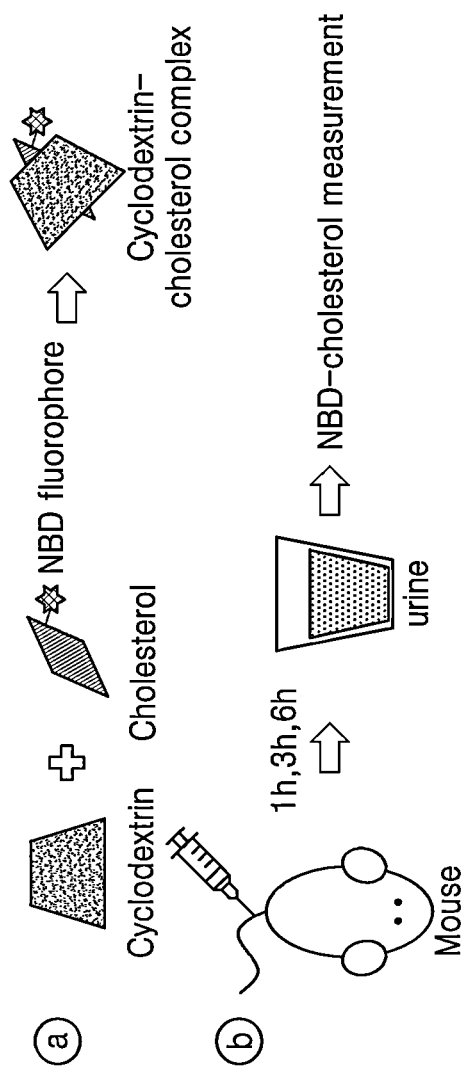
FIG. 6A and FIG. 6B show a scheme (A) describing a) cyclodextrin-cholesterol complex formation and b) its administration into mice for urine collection, and results of renal clearance of cholesterol by different cyclodextrins used for the complex formation (B). Data are mean±SD. *P<0.05, P<0.01, *P<0.001, compared to HPBCD-A; One-way ANOVA analysis and Tukey's multiple comparisons test (n=3).

To investigate the effects on renal clearance of cholesterol, cyclodextrin-cholesterol complex was prepared by mixing 50 mg of cyclodextrins with 1 mg of NBD (2-(4-nitro-2,1,3-benzoxadiazol-7-yl) aminoethyl)-conjugated cholesterol (FIG. 6A, a). The NBD-cholesterol was firstly dissolved in 1-propanol, and then added to the cyclodextrin solution. They were sonicated for 3 minutes and then incubated overnight at room temperature. The solution was freeze-dried and then resuspended in PBS to obtain injectable-form of cyclodextrin-cholesterol complex. Then, the complex solution was intravenously injected into C57BL/7 mice at a cyclodextrin dose of 500 mg/kg. The amount of NBD cholesterol in urine was collected 1, 3, and 6 hours post-injection (FIG. 6A, b).

Figure 6B:
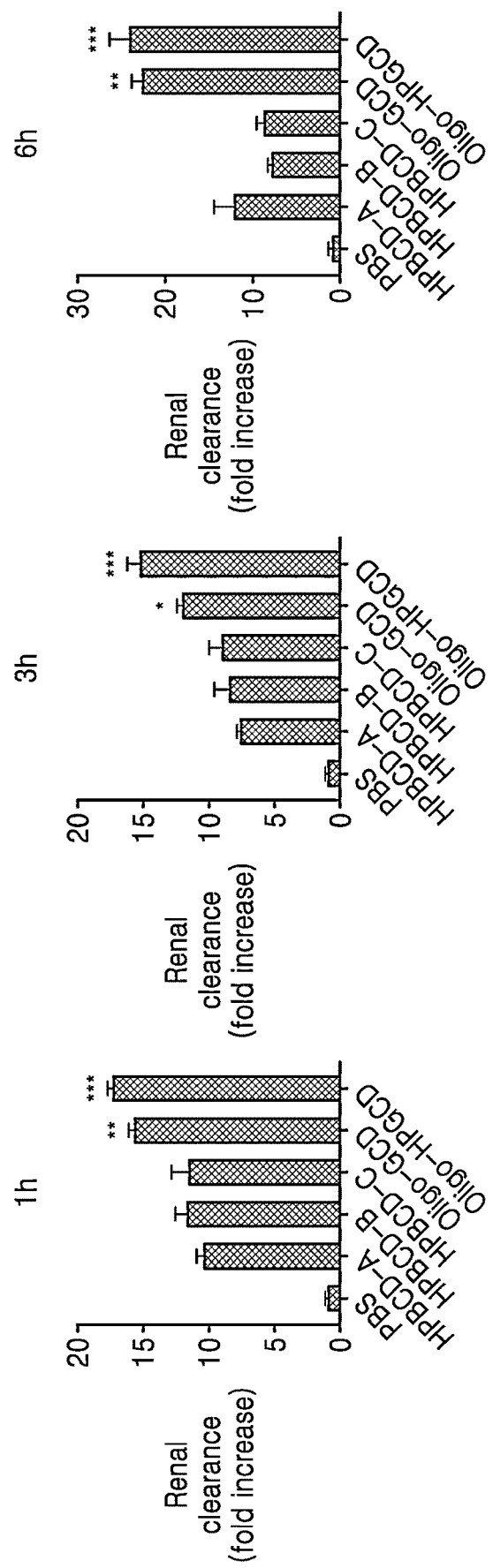

As shown in FIG. 6B, the gamma-cyclodextrin oligomers (Oligo-GCD, Oligo-HPGCD) induced more significant renal clearance of cholesterol at 1, 3, and 6 hours post-injection as compared to HPBCDs (HPBCD-A, HPBCD-B, HPBCD-C). These results show that gamma-cyclodextrin oligomers facilitate renal clearance of cholesterol.

Example 6. Gamma-Cyclodextrin Oligomers with Different Average Molecular Weights To investigate the effects of average molecular weights of gamma-cyclodextrin oligomers on renal clearance of cholesterol, we prepared gamma-cyclodextrin oligomers with different average molecular weights. The amount of NBD-cholesterol in urine was collected 1 and 6 hours post-injection.

Figure 7A:
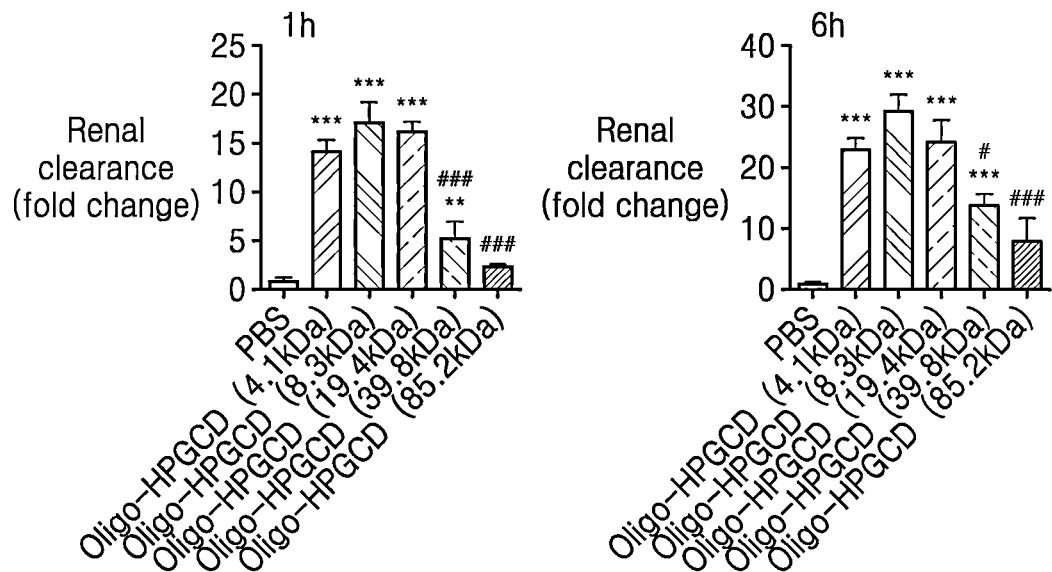
FIG. 7A to FIG. 7c show the effects of average molecular weights of gamma-cyclodextrin oligomers on renal clearance of cholesterol (A, B) and ABCA1 expression and secretion of pro-inflammatory cytokines (C). Data are mean±SD. P<0.01, *P<0.001, compared to Control, #P<0.05, ###P<0.001, compared to Oligo-HPGCD (19.4 kDa) for (A); P<0.01, *P<0.001, compared to Control, &&& <0.001, compared to Oligo-GCD (17.5 kDa) for (B); *P<0.05, P<0.01, *P<0.001, compared to CC for (C); One-way ANOVA analysis and Tukey's multiple comparisons test (n=3).
Figure 7B:
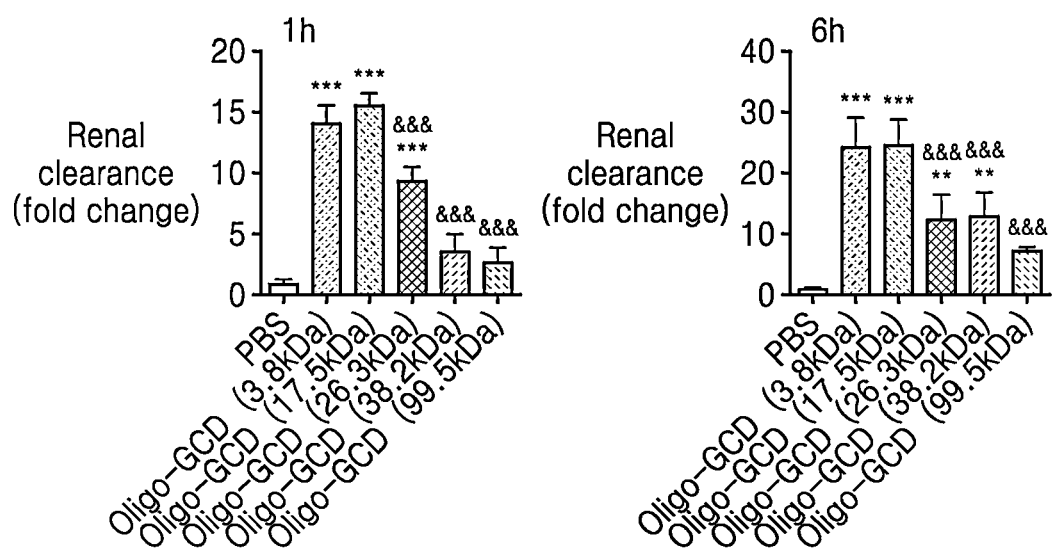

As shown in FIG. 7A and FIG. 7B, the gamma-cyclodextrin oligomers with molecular weights of 4.1 kDa, 8.3 kDa, and 19.4 kDa (Oligo-HPGCD) and 3.8 kDa, and 17.5 kDa (Oligo-GCD) showed the most effective renal clearance of cholesterol. The gamma-cyclodextrin oligomers with larger molecular weights showed compromised renal clearance of cholesterol, plausibly due to reduced glomerular filtration because of their large sizes.

Figure 7C:
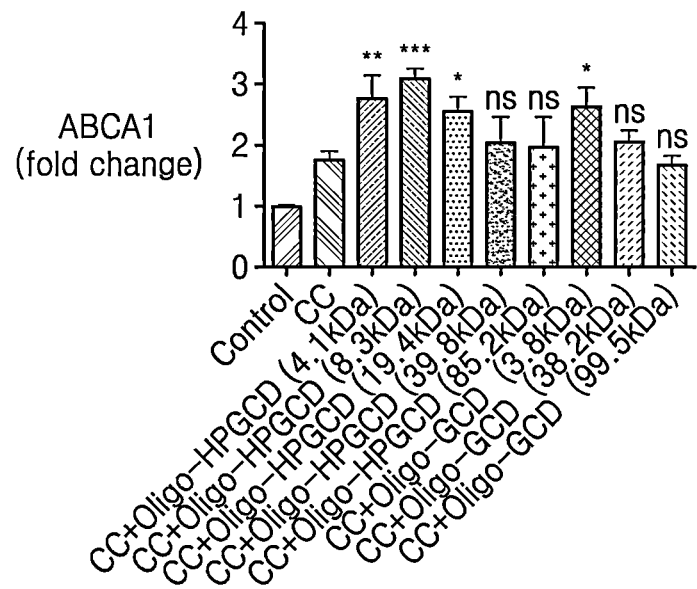
Figure 7C:
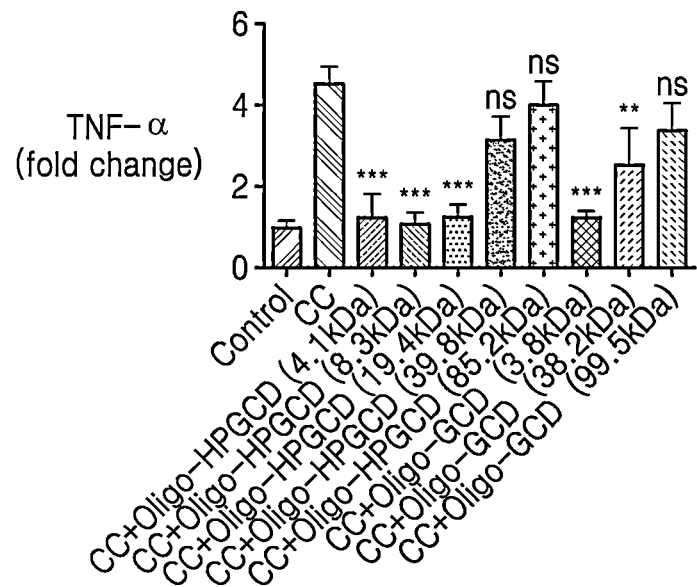

In addition, the effects of average molecular weights of gamma-cyclodextrin oligomers on the expression of ABCA1 and secretion of inflammatory cytokine were studied using the mesangial cells. As shown in FIG. 7C, the gamma-cyclodextrin oligomers with molecular weights of 4.1 kDa, 8.3 kDa, and 19.4 kDa (Oligo-HPGCD) and 3.8 kDa (Oligo-GCD) showed the most effective upregulation of ABCA1 and reduction of secretion of pro-inflammatory cytokine TNF-α in mesangial cells fed with excessive cholesterol. However, the gamma-cyclodextrin oligomers with larger molecular weights showed compromised or no significant effects, showing the importance of using gamma-cyclodextrin oligomers with optimal average molecular weights to maximize its cholesterol modulation and anti-inflammatory effects.

Overall, these results show that the gamma-cyclodextrin oligomers with average molecular weights between 2.5 kDa and 20 kDa, which corresponds to the sizes of oligomers containing approximately 2 to 10 gamma-cyclodextrin monomers, are optimal for facilitating renal clearance of cholesterol, improving cellular cholesterol efflux, and reducing the secretion of inflammatory cytokines induced by cholesterol, while such effects can be compromised or eliminated when the molecular weights of the gamma-cyclodextrin oligomers is out of the range.

Example 7. Effect on Albuminuria in Mouse Model

Figure 8A:
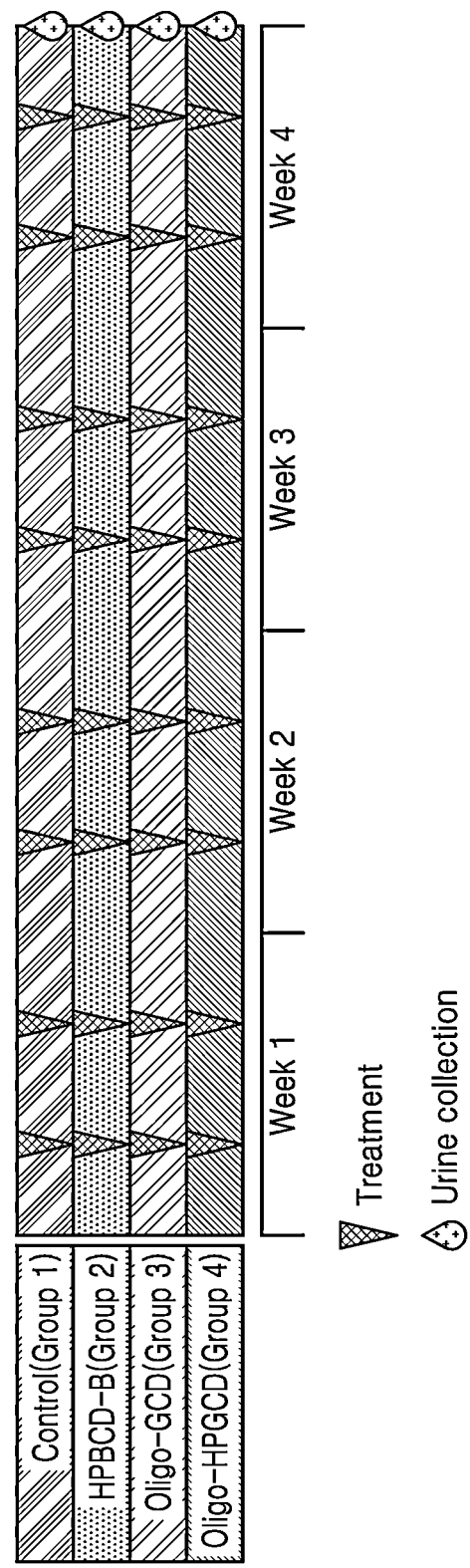
FIG. 8A and FIG. 8B show the effects of gamma-cyclodextrin oligomers and HPBCD on albuminuria in diabetic kidney disease model. 8-week-old male db/db mice were treated with cyclodextrin subcutaneously at a dose of 2 g/kg twice a week for 4 weeks (A). Urine albumin to creatinine ratio (ACR) was determined using the urine samples collected on the last day of week 4 (B). Control mice were treated with PBS only. Data are mean±SD. P<0.01, *P<0.001, compared to Control; One-way ANOVA analysis and Tukey's multiple comparisons test (n=4).

To investigate the effects of cyclodextrins on albuminuria, 8-week-old male db/db mice were used to model diabetes type II, which is susceptible to albuminuria. In the experimental setup, Oligo-GCD (4103 Da), Oligo-HPGCD (3825 Da) and HPBCD-B were subcutaneously injected at a dose of 2 g/kg twice a week for 4 weeks. Control mice were given PBS only. After the treatment is completed, 24-hour urine samples were collected and the concentration of albumin in the urine was measured (FIG. 8A).

Figure 8B:
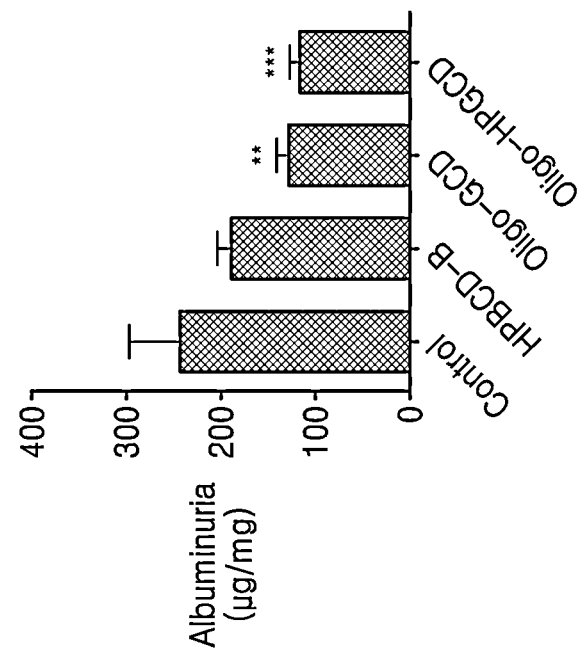

As shown in FIG. 8B, the db/db mice developed significant albuminuria, exhibiting high albumin/creatinine ratio (ACR), which was 246.5 µg/mg. In mice treated with HPBCD-B, the ACR showed nonsignificant decrease to 190.9 µg/mg, which was 22.6% reduction compared to control. In mice treated with Oligo-GCD and Oligo-HPGCD, the ACR showed significant decrease to 129.3 µg/mg and 118.8 µg/mg, which was 47.6% and 51.8% reduction compared to control, respectively. The results show that gamma-cyclodextrin oligomers are effective in reducing albuminuria.

What is claimed is:

1. A method of i) treating, alleviating or reducing albuminuria, ii) reducing an amount of kidney cholesterol, iii) improving renal clearance of cholesterol, and/or iv) treating, alleviating or reducing inflammation in kidney, the method comprising: administering a therapeutically effective amount of gamma-cyclodextrin oligomer to a subject in need thereof, wherein the subject has been diagnosed with or suspected to have a chronic kidney disease,
   wherein an average molecular weight of the gamma-cyclodextrin oligomer is between 2.5 kDa to 20 kDa.

2. The method of claim 1, wherein a level of albumin or albumin to creatinine ratio in urine is reduced by at least about 10% relative to a level of albumin or albumin to creatinine ratio in urine prior to administering the gamma-cyclodextrin oligomer.

3. The method of claim 1, wherein the amount of kidney cholesterol is reduced by at least 10% relative to the amount of kidney cholesterol prior to administering the gamma-cyclodextrin oligomer.

4. The method of claim 1, wherein the renal clearance of cholesterol is improved by at least about 10% relative to renal clearance of cholesterol prior to administering the gamma-cyclodextrin oligomer.

5. The method of claim 1, wherein the gamma-cyclodextrin oligomer comprises gamma-cyclodextrin oligomer species containing at least 2 and at most 10 gamma-cyclodextrin monomers.

6. The method of claim 5, wherein the gamma-cyclodextrin monomer comprises gamma-cyclodextrin or its derivatives,
   wherein the gamma cyclodextrin derivative comprises hydroxypropyl-gamma cyclodextrin.

7. The method of claim 6, wherein the hydroxypropyl-gamma-cyclodextrin has molar substitution value between 0.2 and 0.9.

8. A method of treating chronic kidney disease or one or more symptoms thereof, or reducing a complication related to chronic kidney disease, the method comprising: administering a therapeutically effective amount of gamma-cyclodextrin oligomer to a subject in need thereof, wherein an average molecular weight of the gamma-cyclodextrin oligomer is between 2.5 kDa to 20 kDa.

9. The method of claim 8, wherein the treating comprises i) treating, alleviating or reducing albuminuria, ii) reducing an amount of kidney cholesterol, iii) improving renal clearance of cholesterol, and/or iv) treating, alleviating or reducing inflammation in kidney of the subject.

10. The method of claim 8, wherein the gamma-cyclodextrin oligomer comprises gamma-cyclodextrin oligomer species containing at least 2 and at most 10 gamma-cyclodextrin monomers.

11. The method of claim 10, wherein the gamma-cyclodextrin monomer comprises gamma-cyclodextrin or its derivatives,
wherein the gamma cyclodextrin derivative comprises hydroxypropyl-gamma cyclodextrin.

12. The method of claim 11, wherein the hydroxypropyl-gamma-cyclodextrin has molar substitution value between 0.2 and 0.9.

13. The method of claim 8, wherein the therapeutically effective amount is from about 20 mg/kg to about 4,000 mg/kg, or from about 1 g to about 200 g.

14. The method of claim 8, wherein the therapeutically effective amount is an amount sufficient to achieve a serum, plasma, and/or whole blood concentration of gamma-cyclodextrin oligomer of about 0.01 mg/ml to about 20 mg/ml.

15. The method of claim 8, wherein the administering is conducted by intravenous, subcutaneous, intramuscular, or intraperitoneal injection.

16. The method of claim 15, wherein the administering is conducted using a wearable injection device.

17. The method of claim 8, wherein the administering further comprises: (i) administering, at a first time point, a therapeutically effective first dose of gamma-cyclodextrin oligomer to the subject; and (ii) administering, at a second time point, a therapeutically effective second dose of gamma-cyclodextrin oligomer to the subject.

18. The method of claim 17, wherein the second time point is at least 6 hours, at least 12 hours, at least 1 day, at least 2 days, at least 3 days, at least 4 days, at least 5 days, at least 6 days, at least a week, at least 2 weeks, at least 3 weeks, at least 4 weeks, at least 2 months, at least 3 months, at least 6 months, or at least 12 months after the first time point.

19. The method of claim 8, wherein the administering further comprises administering every day, every 3 days, every 7 days, every 10 days, every 14 days, every 21 days, every 28 days, every 2 months, every 3 months, every 6 months, every 12 months.

20. A method of i) reducing ACE inhibitors, angiotensin II receptor blockers (ARBs), calcineurin inhibitors (CIs), or steroids treatment, or ii) reducing a frequency or delaying renal replacement therapy, or iii) delaying a kidney transplant in a subject diagnosed with or suspected to have chronic kidney disease, the method comprising: administering a therapeutically effective amount of gamma-cyclodextrin oligomer to the subject,
wherein an average molecular weight of the gamma-cyclodextrin oligomer is between 2.5 kDa to 20 kDa.

21. The method of claim 20, wherein the gamma-cyclodextrin monomer comprises gamma-cyclodextrin or its derivatives,
wherein the gamma cyclodextrin derivative comprises hydroxypropyl-gamma cyclodextrin.

22. The method of claim 20, wherein the ACE inhibitors, ARBs, CIs, or steroids treatment is reduced at least by 20% compared to before administering the gamma-cyclodextrin oligomer.

23. The method of claim 20, wherein the frequency of renal replacement therapy is reduced at least by 20% compared to before administering the gamma-cyclodextrin oligomer, or wherein the initiation of renal replacement therapy is delayed at least 6 months.

24. The method of claim 20, wherein the kidney transplant is delayed at least 6 months.

* * * * *